(12) United States Patent
Ntziachristos et al.

(10) Patent No.: US 11,596,312 B2
(45) Date of Patent: Mar. 7, 2023

(54) DEVICE AND METHOD FOR OPTOACOUSTIC IMAGING OF AN OBJECT

(71) Applicant: HELMHOLTZ ZENTRUM MUENCHEN DEUTSCHES FORSCHUNGSZENTRUM etc., Neuherberg (DE)

(72) Inventors: Vasilis Ntziachristos, Graefelfing (DE); Juan Aguirre Bueno, Munich (DE)

(73) Assignee: Helmholtz Zentrum München Deutsches Forschungszentrum für Gesundheit und Umwelt (Gmbh), Neuherberg (DE)

(*) Notice: Subject to any disclaimer, the term of this patent is extended or adjusted under 35 U.S.C. 154(b) by 347 days.

(21) Appl. No.: 15/309,547

(22) PCT Filed: May 12, 2015

(86) PCT No.: PCT/EP2015/060490
§ 371 (c)(1),
(2) Date: Nov. 8, 2016

(87) PCT Pub. No.: WO2015/177001
PCT Pub. Date: Nov. 26, 2015

(65) Prior Publication Data
US 2017/0156600 A1 Jun. 8, 2017

(30) Foreign Application Priority Data
May 20, 2014 (EP) .................................... 14001778

(51) Int. Cl.
*A61B 5/00* (2006.01)
(52) U.S. Cl.
CPC .......... *A61B 5/0095* (2013.01); *A61B 5/0077* (2013.01); *A61B 5/441* (2013.01)

(58) Field of Classification Search
None
See application file for complete search history.

(56) References Cited

U.S. PATENT DOCUMENTS

| 4,227,417 A | 10/1980 | Glenn |
| 44,664,444 | 8/1984 | Baba |

(Continued)

FOREIGN PATENT DOCUMENTS

| WO | WO 2010/005116 | 1/2010 |
| WO | WO 2011/152747 | 12/2011 |

(Continued)

OTHER PUBLICATIONS

Burgholzer et al: "Spatial resolution and sensitivity in photoacoustic tomography taking noise into account: From point-like detectors to large integrating detectors", Progress in Biomedical Optics and Imaging—Proceedings of SPIE—Photons Plus Ultrasound: Imaging and Sensing 2012 2012 SPIE USA, vol. 8223, 2012, XP002726814.

(Continued)

*Primary Examiner* — Shahdeep Mohammed
(74) *Attorney, Agent, or Firm* — Sheridan Ross P.C.

(57) ABSTRACT

The invention relates to a device (1) and an according method for optoacoustic imaging of an object. The device (1) comprising an irradiation unit for irradiating a region of interest (3) of the object with electromagnetic radiation (6), in particular light, and a detection unit (9) for detecting acoustic, in particular ultrasonic, waves generated in the region of interest (3) of the object upon irradiation with the electromagnetic radiation (6), wherein the detection unit (9) is configured to detect the acoustic waves at one or more point-like detection locations, which are located outside of the region of interest (3) of the object. The point-like detection locations can be given by, e.g., focus points (19) of acoustic detection elements (23), point-like detection elements or point-like or pinhole apertures. The invention (Continued)

allows for improved and reliable optoacoustic imaging, in particular in view of dermatology applications.

19 Claims, 13 Drawing Sheets

(56) References Cited

U.S. PATENT DOCUMENTS

| | | | |
|---|---|---|---|
| 5,348,002 A | 9/1994 | Caro | |
| 6,216,540 B1* | 4/2001 | Nelson | A61B 5/0091 |
| | | | 73/633 |
| 7,322,972 B2 | 1/2008 | Viator et al. | |
| 8,323,201 B2* | 12/2012 | Towfiq | A61B 5/7264 |
| | | | 600/459 |
| 2006/0184042 A1* | 8/2006 | Wang | A61B 5/0073 |
| | | | 600/476 |
| 2009/0005685 A1 | 1/2009 | Nagae et al. | |
| 2011/0087107 A1* | 4/2011 | Lindekugel | A61B 8/4281 |
| | | | 600/461 |
| 2011/0088477 A1* | 4/2011 | Someda | A61B 5/0095 |
| | | | 73/641 |
| 2011/0190617 A1 | 8/2011 | Chen | |
| 2012/0190963 A1* | 7/2012 | Fukutani | G01N 21/1702 |
| | | | 600/407 |
| 2013/0039147 A1 | 2/2013 | Witte et al. | |
| 2013/0190591 A1* | 7/2013 | Hirson | A61B 5/0095 |
| | | | 600/407 |
| 2013/0286778 A1* | 10/2013 | Kisner | G01S 15/89 |
| | | | 367/35 |
| 2014/0005544 A1* | 1/2014 | Zalev | A61B 5/0095 |
| | | | 600/440 |

FOREIGN PATENT DOCUMENTS

| | | |
|---|---|---|
| WO | WO 2013/167147 | 11/2013 |
| WO | WO 2014/156408 | 10/2014 |

OTHER PUBLICATIONS

Chen et al: "Low-noise small-size microring ultrasonic detectors for high-resolution photoacoustic imaging.", Journal of Biomedical Optics May 2011, vol. 16, No. 5, May 2011 (May 2011), p. 56001, XP060013525.

International Search Report and Written Opinion prepared by the European Patent Office dated Sep. 10, 2015, for International Application No. PCT/EP2015/059545.

"Piezoelectric Components: Ultrasonic Transducers," Boston Piezo-Optics, as of Sep. 2018, 4 pages [retrieved online from: www.bostonpiezooptics.com/the-ultrasonic-transducer].

"Ultrasonic Transducers Technical Notes," Olympus NDT, 2006, 11 pages.

Deng et al. "Two-dimensional synthetic-aperture focusing technique in photoacoustic microscopy," Journal of Applied Physics, 2011, vol. 109, 104701, 6 pages.

Szabo "Diagnostic Ultrasound Imaging: Inside Out," Elsevier Inc., 2004, pp. 154-163.

Li et al., "High-numerical-aperture-based virtual point detectors for photoacoustic tomography," Applied Physics Letters, 2008, vol. 93 (033902), 3 pages.

Li et al., "Improved in vivo photoacoustic microscopy based on a virtual-detector concept," Optics Letters, 2006, vol. 31(4), pp. 474-476.

Maslov et al., "In vivo dark-field reflection-mode photoacoustic microscopy," Optics letters, 2005, vol. 30(6), pp. 625-627.

* cited by examiner

Fig. 3
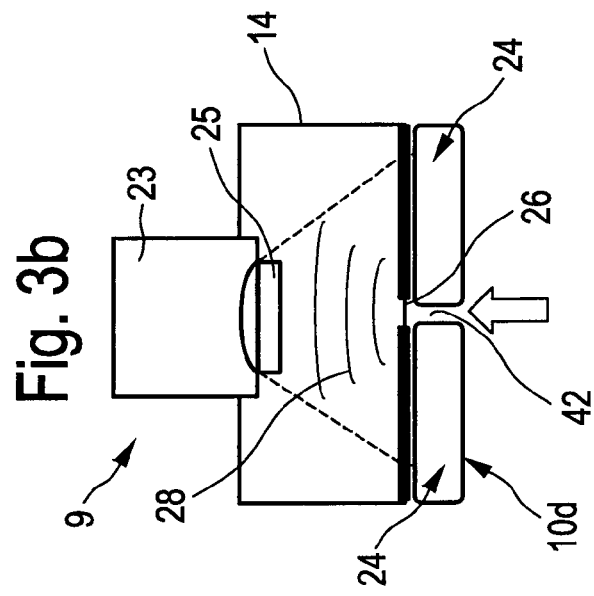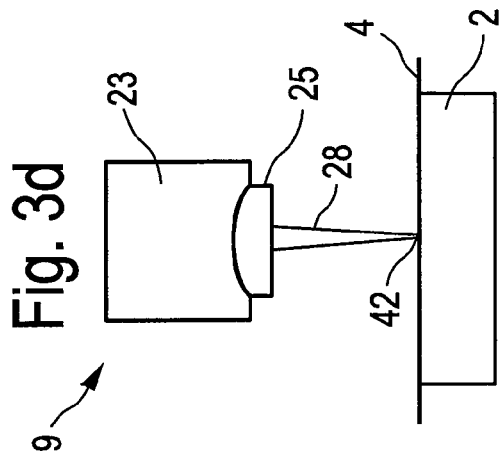
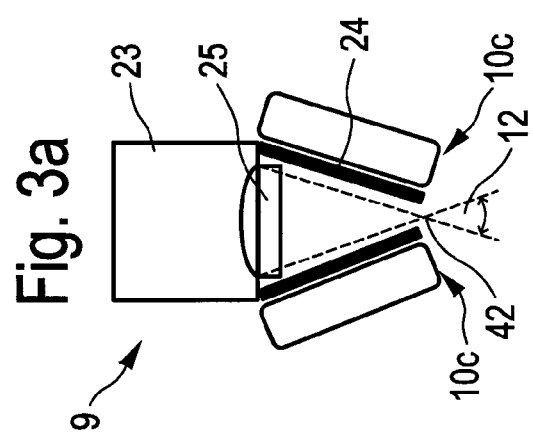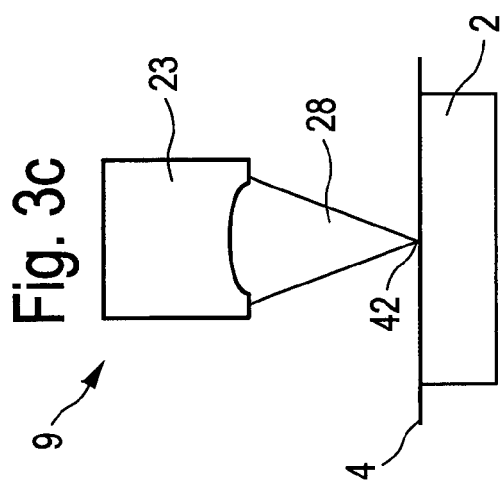

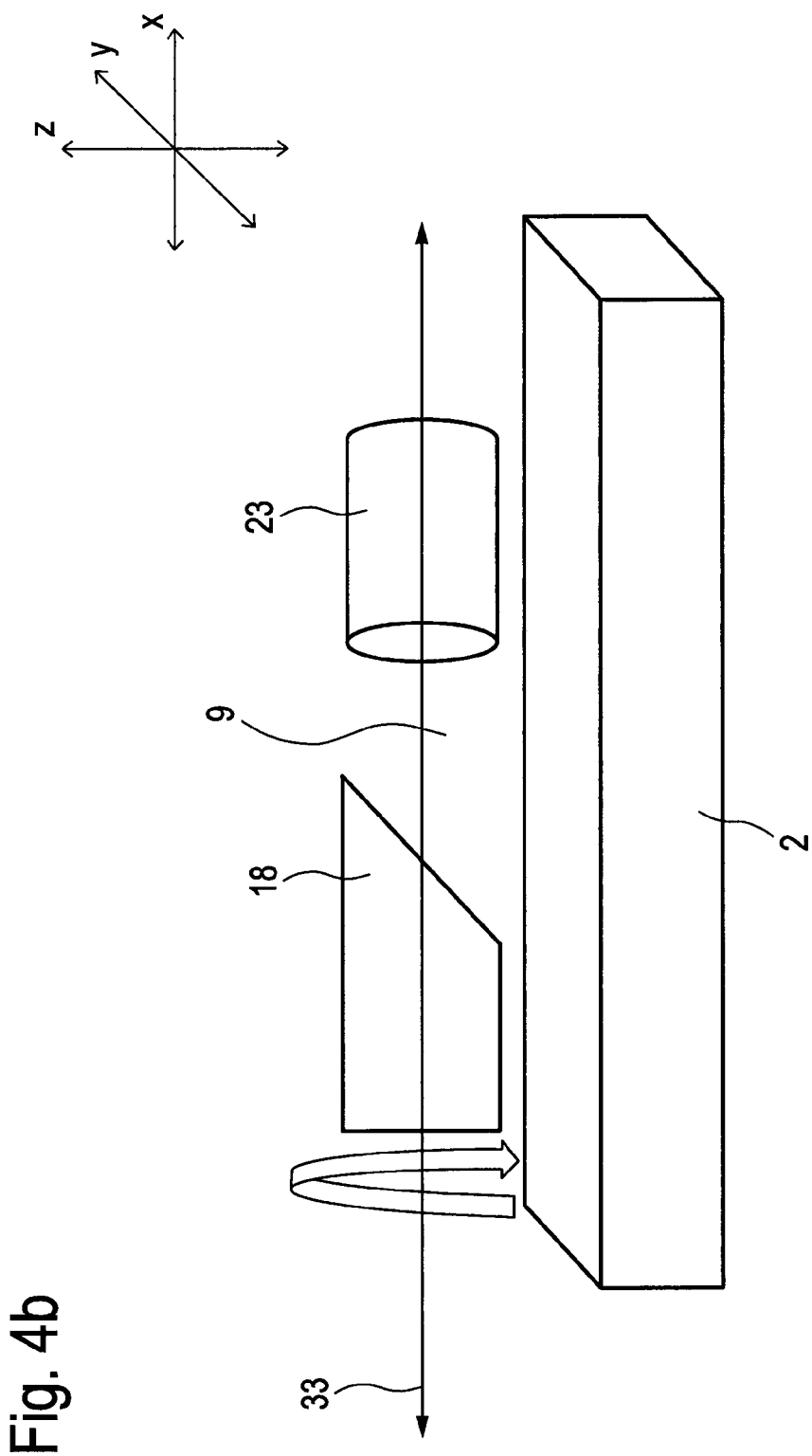

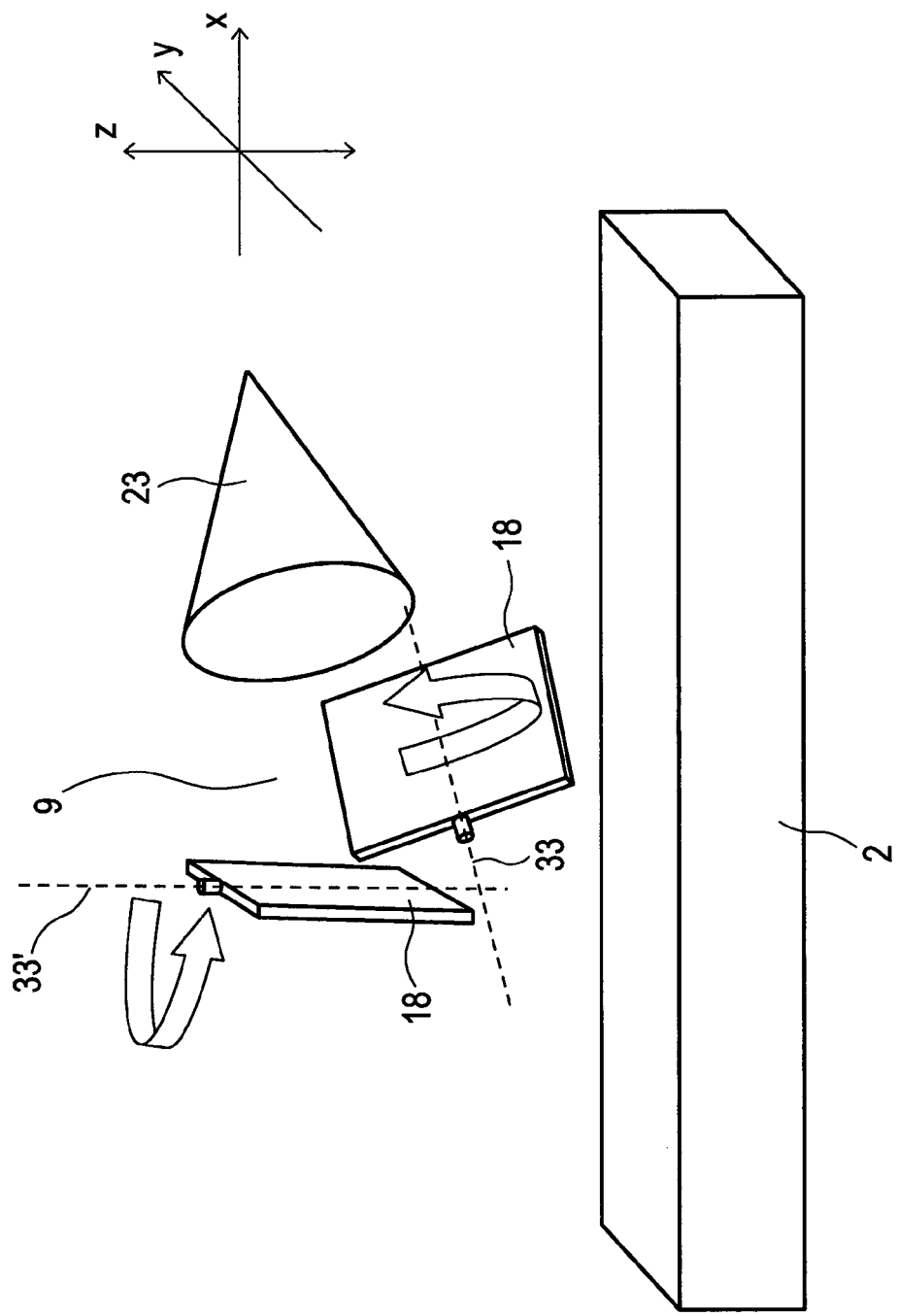

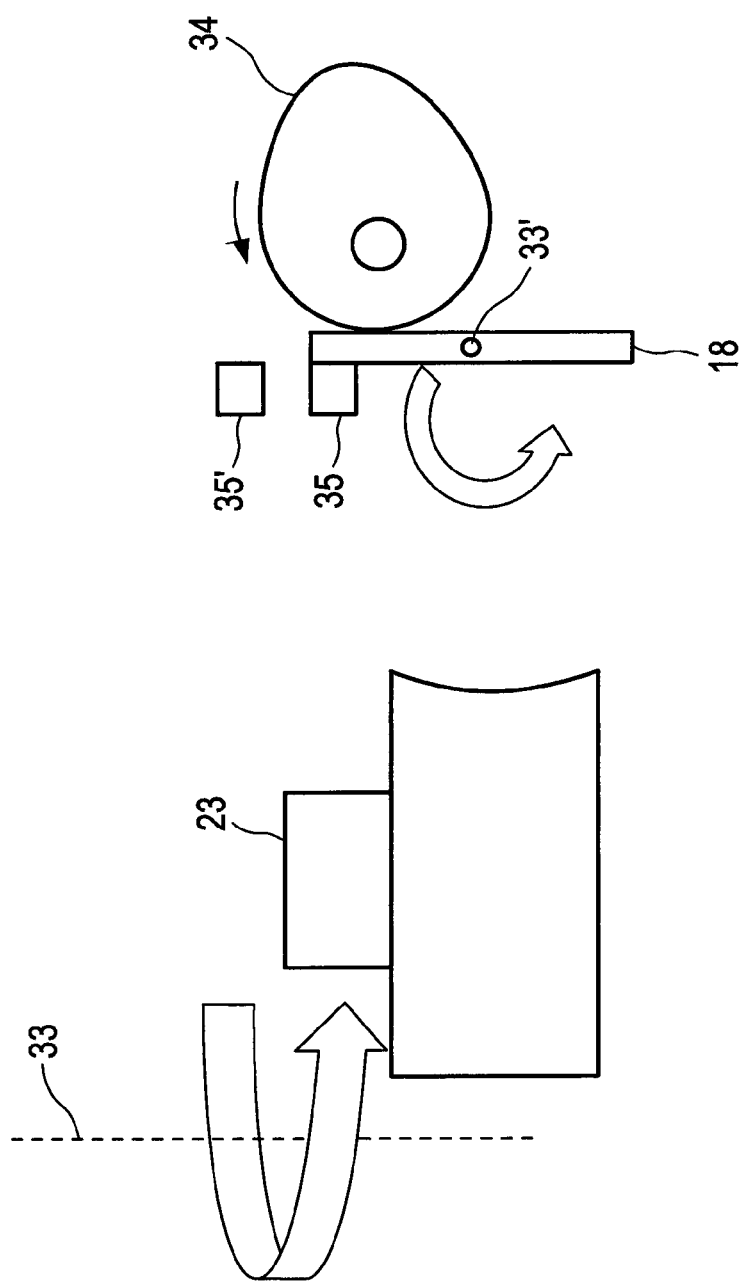

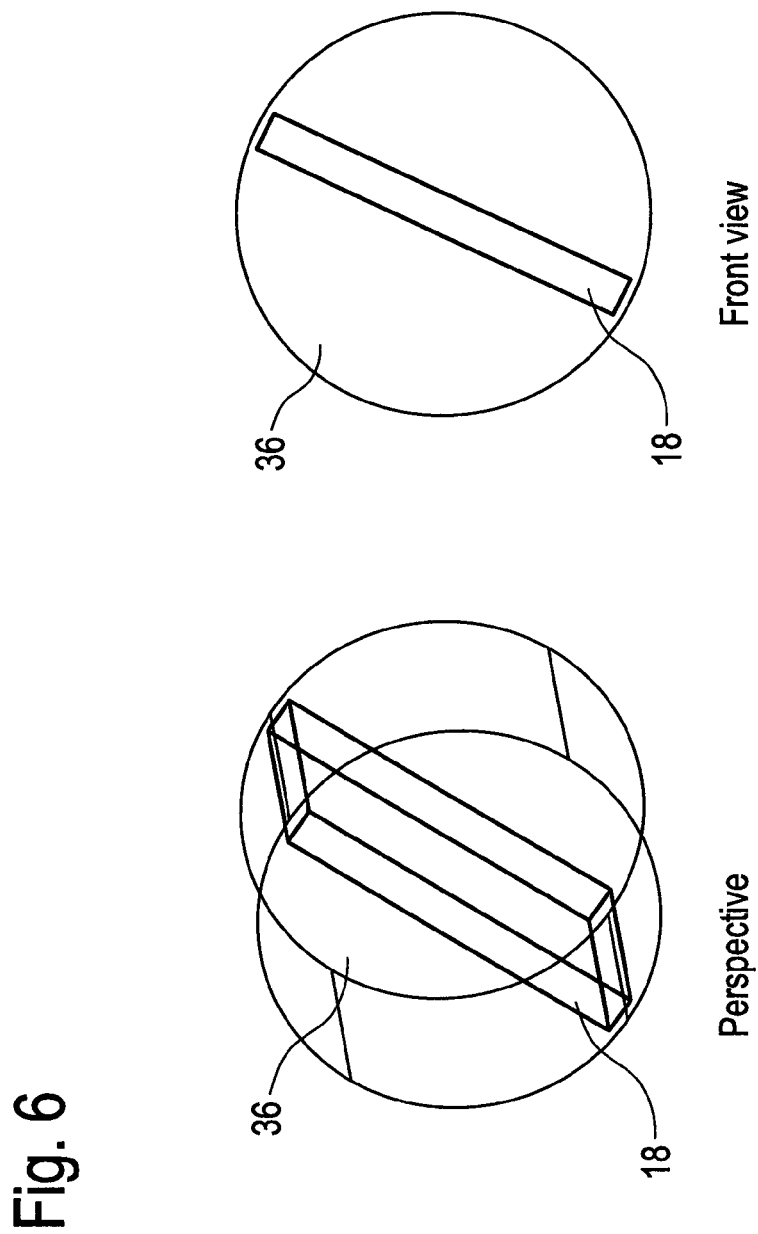

DEVICE AND METHOD FOR OPTOACOUSTIC IMAGING OF AN OBJECT

CROSS REFERENCE TO RELATED APPLICATIONS

This application is a national stage application under 35 U.S.C. 371 and claims the benefit of PCT Application No. PCT/EP2015/060490 having an international filing date of 12 May 2015, which designated the United States, which PCT application claimed the benefit of European Patent Application No. 14001778.1 filed 20 May 2014, the disclosure of each of which are incorporated herein by reference in their entireties.

The present invention relates to a device and a method for optoacoustic imaging of an object according to the independent claims.

Optoacoustic imaging is based on the photoacoustic effect, according to which ultrasonic waves are generated due to absorption of electromagnetic radiation by an object, e.g. a biological tissue, and a subsequent thermoelastic expansion of the object. Excitation radiation, for example laser light or radiofrequency radiation, can either be pulsed radiation with short pulse durations or continuous radiation with a modulated amplitude or frequency.

Optoacoustic imaging of biological tissues provides a unique combination of high spatial resolution and rich contrast based on spectrally-dependent absorption of light. Techniques like multispectral optoacoustic tomography (MSOT) are therefore able to simultaneously render images of anatomical, functional and molecular contrast by exciting tissues at several optical wavelengths, thereby enabling highly promising applications in molecular imaging and diagnostics, drug development and treatment monitoring.

It is an object of the invention to provide a device and a method allowing for an improved and reliable optoacoustic imaging of an object, in particular a device and method appropriate for dermatology and/or epithelial tissue imaging applications in terms of resolution interfacing to the skin/epithelial tissue dimensions, portability and form factor, i.e. a device with design and/or physical dimensions appropriate for portable dermatology or endoscopic applications.

This object is achieved by a device and a method according to the independent claims. Advantageous embodiments of the invention are defined in the dependent claims.

A device according to a preferred embodiment of the invention comprises an irradiation unit for irradiating a region of interest of the object with electromagnetic radiation, in particular light, and a detection unit for detecting acoustic, in particular ultrasonic, waves generated in the region of interest of the object upon irradiation with the electromagnetic radiation, wherein the detection unit is designed for detecting the acoustic waves at one or more point-like detection locations, which are preferably located outside of the region of interest of the object.

In a method according to a preferred embodiment of the invention a region of interest of the object is irradiated with electromagnetic radiation, in particular light, by means of an irradiation unit and acoustic, in particular ultrasonic, waves are detected, which were generated in the region of interest of the object upon irradiation with the electromagnetic radiation. Further, the acoustic waves are detected at one or more point-like detection locations, which are preferably located outside of the region of interest of the object. The term "detection location" within the meaning of the present invention preferably relates to a location at which acoustic waves are directly detected, e.g. by an acoustic detector located at the detection location, and/or to a real or virtual location which acoustic waves can pass through for being subsequently detected by an acoustic detector. Accordingly, detection locations in the sense of the present invention may be formed in different manners, for example by providing point-like acoustic detection elements at the detection locations, by providing one or more detection elements with one or more focus points, wherein each of the focus points being located at a detection location, or by providing one or more point-like apertures, wherein each of the point-like apertures being located at a detection location.

It has to be noted that within the meaning of the present invention the term "optoacoustic imaging" is not limited to optoacoustic imaging within the narrower sense, i.e. where the object is irradiated with visible light, but also relates to photoacoustic imaging and thermoacoustic imaging, where the object under investigation is irradiated with electromagnetic radiation in other spectral ranges, e.g. the radiofrequency or microwave range.

The detection locations are established preferably with the ultrasound equivalent of an optical pinhole, i.e. detecting waves passing through one small real or virtual aperture. The aperture accepts sound waves passing through the aperture and rejects and/or does not detect waves propagating in other directions not passing through the pinhole. This operation can be established by physical means (e.g. by small physical detectors, small sound apertures, needle sound carriers embedded in low-transmitting sound material) or by virtual means implemented using acoustic lenses, detectors of particular shape to reject signals or detector arrays. An advantageous aspect associated with pinhole detection relates to measures that ensure wide-angle acceptance of ultrasonic waves as disclosed in the preferred embodiments.

The term "point-like" referring to detection locations within the meaning of the present invention preferably relates to small-sized sound detection entities, like small-sized ultrasound transducers, apertures, pinholes or detection focal points, the size of which is in the range, in particular in the same order or smaller of the achievable and/or desired spatial resolution of an image to be obtained using the device and/or the method according to the invention. While the pinhole size will determine the lateral resolution achieved, high-axial resolution can be similarly implemented by adapting the detection frequency of the detector to several tens of MHz or hundreds of MHz for achieving axial resolution below 30 micrometers, preferably below 10 micrometers.

The invention is based on the approach to provide a device for optoacoustic imaging of an object having a detection unit, which is designed to detect the acoustic waves at one or more point-like detection locations, wherein the point-like detection locations are located outside of the region of interest of the object, preferably on or above a surface of the object under investigation. The point-like detection locations may be given by different entities, for example one or more point-like sound detection elements, one or more focus points of one or more sound detection elements, or one or more point-like apertures to be passed by acoustic waves before being subsequently detected by a sound detector. A point-like detector is assumed to be a small aperture area, which can be symmetric or asymmetric and can be of circular, rectangular or any other shape. Preferably the size of the point detector is at least comparable in size or smaller than the desired spatial resolution.

Due to the point-like character of sound detection, a high spatial certainty regarding the detected acoustic information and, therefore, a high sharpness of the obtained images can be achieved. Conversely, no directional certainty is afforded by these detectors. In other words it is not possible to determine with pinhole detectors the exact angle or angles that a certain sound comes from along one, two or three dimensions. To resolve this issue, the device preferably employs image formation based on tomographic principles and may employ modelling of the tomographic detection process by assuming a known sensitivity field, i.e. a spatial distribution of the relative strength and/or dispersion by which an acoustic source in the tissue is detected at the at least one point-like detection entity. The sensitivity field can be employed to weigh reconstructions based on back-projection or model based inversion approaches, for example by as-signing certain weights to data modelled along certain directions or data associated with certain locations in space.

Another aspect is that the usage of a plurality of point-like detection locations, which can be arranged in a two-dimensional grid, may yield high resolution images, since a high number of space-resolved data is collected and converted to tomographic images. The grid assumed herein could be a flat grid or a grid assuming a curvature, the latter possibly improving the image quality assumed. The detector locations can form a pattern in space in a time-invariant or a time-dependent manner, e.g. through arrays of detectors or by translation of detector elements.

Still another aspect is that the use of point-like detection locations may improve tomographic approaches, like model based inversion schemes, in particular when a point-spread-function (PSF) correction, also known as impulse response correction, is incorporated. This can be achieved, when using model based inversion schemes, whereby the physical process of a real detector provided at detection locations is modelled instead of idealizing the detector as a single point. In this respect, the physical dimensions of the detector employed are incorporated in the inversion model during a process that either integrates signal detection over the entire detector aperture or uses an equivalent process. Therefore, providing point-like detection locations according to the invention allows for both a simplification and an improvement of tomographic image reconstruction. Alternatively, it is possible to deploy deconvolution in order to account for the physical or virtual dimensions of the pinhole and improve the image resolution and/or quality. Deconvolution can be applied in two or three-dimensions according to methods disclosed in the literature.

By detecting acoustic waves according to the invention, the data to be collected are well suited for achieving high resolution images, for instance in the field of epithelial tissue imaging, such as the skin, in the mesoscopics range, i.e. at depths up to a few millimeters. This may preferably be achieved using a variety of tomographic conversion approaches including back-projection algorithms or model based approaches, such as forward modelling.

Last but not least, the invention relates to arrangements that impart a small form factor and portable, easy to use handheld operation which enables seamless integration into the operating room. At the core of the device design is the use of a light-weight technology which enables fast measurement of out-of-focus ultrasonic signals in order to quickly collect multi-projection data from tissue. Fast processing operations preferably further allow a real time representation of the scanned data for direct feedback to the physician. Portability in particular refers to a form factor that can allow operation by a single hand/arm of an operator using light-weight and small form factor machinery. This is achieved herein by using small form factor detectors and flexible optical guidance systems for illumination. Although the detector unit is on the handheld part of the device, the light source and the detection and computation electronics could be placed in a control unit which is separate from the handheld part.

Portability herein further implies that the arrangement of pinhole detectors is done in such a way that at least the detector pattern and at least part of the illumination arrangement is enclosed into one unit (see, e.g., FIGS. 1 and 1A which will be discussed in detail below) which possibly integrates several other systems, including an optical system for visual inspection, a fluorescence imaging system, an optical coherence tomography system or an optical resolution optoacoustic microscopy system.

A particularly preferred inventive feature herein is that the portable device effectively places the point-like detection locations (pinhole detectors) in an invariable distance to the object surface. Invariable distance is defined herein in the sense that the distance between the pinhole detector pattern and the surface of the object imaged does not change through the data acquisition process. To achieve this, the device implements the pinhole detector pattern using an effective surface, also referred to as "intermediate surface", determined by the front part of the device. i.e. the side of the device directed towards the object, which is congruent with the direction of sound detection. This side establishes direct contact with the object of interest. Direct contact is defined herein either as direct physical contact of the device and the object, or through an acoustically matching spacer or medium. In all cases, the effective surface is established between the device and the object, connects the device and the object and has the crucial role of establishing 1) a barrier between the device machinery and the tissue imaged, (barrier preventing electrical, fluid or other flow from one medium to the other) and 2) a reference point between the pinhole detector(s) and the surface of the object. The reference point is preferably required in the sense of preventing the movement of the object surface and of the object imaged in relation to the pinhole detector pattern during the acquisition. This is particularly advantageous in handheld operation. The device proposed herein preferably achieves resolutions in the order of 1-50 microns. However, handheld operation can easily move the scanner by distances that are orders higher than the desired resolution. The establishment of the effective surface fixes or locks the object imaged in relation to the portable scanner, so that movements of the scanner are translated to the object imaged. In this manner the relative distance between the pinhole detectors and the object imaged does not change during the scan, as long as direct contact through the effective surface is applied.

Handheld operation is advantageous for accessing all body parts in a physician's office or an out-patient examination. Different methods are foreseen for establishing the effective surface for the portable opto-acoustic device, as opposed to a stationary scanner. The inventive device foresees the use of a border or "rim" in the front end of the device that slightly compresses the tissue under investigation, keeping it immovable in relation to the detector. In addition or alternatively, this operation is enabled by using an effective surface made of material that establishes friction between the device and the object imaged, for example the skin. Finally, a suction operation may be provided where the device further generates negative pressure to force the skin or other epithelial tissue to attach to the front end of the device using a manually operated or mechanically/electronically operating pump in analogy to the suction action of an octopus suction cup. It is to be understood that the effective surface could be a membrane, separating the pinhole detectors from the object, possibly further enclosing a coupling medium for sound coupling to the detectors. This membrane could then be in direct contact with the object imaged. Alternatively, the effective surface could be the bare surface of a cMUT wafer or piezoelectric detector array and of the illumination unit, manufactured to create a physical surface acting as the effective surface in direct contact with the object. A further alternative would be an effective surface generated by a protective membrane placed in front of a detection pattern, for example in front of a cMUT wafer or piezoelectric detector array. The effective surface could serve yet another function, in particular to enclose an acoustic matching medium that couples sound from the object to the ultrasound detector. This could be a solid, gel or fluid material contained within the enclosure and prevented from escaping by a membrane also establishing the effective surface.

In particular, it is also possible to integrate the light sources onto the portable head (light emitting diodes, laser diodes). In this case it is further possible to achieve data transfer wirelessly, i.e. through transmission and detection of radiowaves, microwaves or light. This can be achieved in particular when using intensity modulated, frequency modulated or phase modulated light. For multi-spectral imaging, light sources of different wavelengths need to be incorporated. Alternatively, a light guide is guiding light from a light source placed elsewhere to minimize the weight of the device especially when light pulses are used; the latter requiring larger sources.

In summary, the invention allows for a reliable acquisition of high-quality optoacoustic images of an object and in particular fulfills the resolution needs with respect to the examination of skin and endothelial tissues.

In a preferred embodiment, the point-like detection locations are located on a surface of the object. In particular, when detecting optoacoustic waves, the device is in contact with the object. By this means, high resolution images can be received also for sections of the object, which correspond to regions of interest at larger depths beneath the surface of the object. Further, only a thin film of coupling medium between the object and the device may be sufficient to perform efficient acoustic and/or optical coupling.

In a further preferred embodiment, the point-like detection locations are located above a surface of the object. Preferably, the point-like detection locations are located in the proximity of the surface of the object, in particular at a distance of less than 2 mm, in particular less than 1 mm, from the surface of the object. By these means, a spacing is obtained between the point-like detection locations and the surface of the object. Preferably, a coupling medium is provided to fill the space created between the scanner and the surface of the object imaged. Advantageously, the spacing allows for coupling electromagnetic radiation, in particular light, into the object from a side area of the device, also referred to as side illumination, instead of or in addition to an illumination from a direction above the object, also referred to as front illumination. Moreover, in the case of having a spacing which is filled with coupling medium, the device can be easily and safely moved on or over the object without the risk of scratching or damaging the point-like detection locations of the detection unit.

In another preferred embodiment, each of the one or more point-like detection locations exhibits a field of view, in particular a divergent field of view, in which acoustic waves are collected. In this way, a large portion of the emitted acoustic energy from the object imaged is collected by the device, even though individually sound is detected by small-sized sound detection entities, like small-sized ultrasound transducers, apertures or pinholes.

According to a further embodiment of the invention, the detection unit comprises one or more point-like detection elements located at said point-like detection locations for detecting acoustic waves. The term "detection elements" within the meaning of the present invention relates to any sound detection elements, which are preferably located at said point-like detection locations for detecting acoustic waves and which are in particular arranged on a one- or two-dimensional array, which is located at said point-like detection locations, for detecting acoustic waves. The term "point-like" referring to the term "detection elements" preferably relates to small-sized detection elements, the size of which is in the range, in particular in the same order, of the desired and/or achievable spatial resolution, in particular the lateral resolution, of the image to be obtained. By this means, the acoustic waves can be directly detected at the one or more point-like detection locations without providing an additional setup. This may simplify the device and reduce its costs.

In a particularly preferred embodiment, the point-like detection elements comprise sensitive areas, which have dimensions smaller than 150 μm, in particular smaller than 50 μm. By this means, spatial certainty regarding the detected acoustic information is further improved and, therefore, the sharpness of the obtained images is further enhanced. Moreover, a high number of detection elements can be implemented in a detection unit. Therefore, a high number of space-resolved, optoacoustic data can be collected in parallel, which may further improve the acquisition of high resolution images using tomographic approaches, such as back-projection algorithms or model based approaches.

Preferably, the detection unit comprises a plurality of point-like detection elements, which are arranged on a one- or two-dimensional pattern. For detecting acoustic waves, said one- or two-dimensional pattern is established by an array of detectors and is located at said point-like detection locations. By this means, multiple data points, which are arranged in a one- or two-dimensional grid, can be collected. These data can then be converted to high resolution images using tomographic approaches, such as back-projection or model based approaches, which may improve high-resolution images.

In another particularly preferred embodiment, the point-like detection elements correspond to capacitive ultrasonic transducers, in particular capacitive micromachined ultrasonic transducers (CMUTs). CMUTs are transducers, wherein the energy transduction is due to change in capacitance. Preferably, CMUTs are constructed on silicon using micromachining technique, wherein a cavity is formed in a silicon substrate, and a thin layer suspended on the top of the cavity serves as a membrane on which a metallized layer acts an electrode, together with the silicon substrate which serves as a bottom electrode. If an AC signal is applied across the biased electrodes, it will generate ultrasonic waves in the medium of interest. In this way, a CMUT works as a transmitter. On the other hand, if ultrasonic waves are applied on the membrane of biased CMUT, as with the present preferred embodiment of the invention, it will generate alternating signal as the capacitance of the CMUT is varied. In this way, it works as a receiver of ultrasonic waves. Compared to other transducer techniques, by means of using CMUTs as point-like detection elements a considerably large number of transducers can be included in a transducer array.

According to another preferred embodiment, the one or more point-like detection locations correspond to one or more focus points of one or more detection elements for detecting acoustic waves. Preferably, the detection elements correspond to focused ultrasound transducers having an ultrasound sensitivity exhibiting a maximum at some distance from the transducer face. In the focal zone of the transducer, the ultrasound sensitivity may be heightened by 100 times or more compared with the sensitivity outside of the focal zone. Because of this increased sensitivity, a much larger acoustic signal will be obtained from a sound emitting entity when being positioned in the focal zone.

Another preferred inventive aspect herein is the use of ultra-wide band ultrasound frequencies, using broadband detectors, for deploying further advantageous capabilities of the technology presented herein. Several energy absorbing features in epithelial tissues have different sizes, which correspondingly emit sound at different frequencies. Detection of these frequencies over a broad frequency band is particularly beneficial as it allows visualization of different tissue features ranging from small vessels (venules, arterioles) to larger vessels and interfaces or other tissue structures. It was found that broadband spectra can be achieved by using material from a Lithium Niobate (LiNbO3) crystal, which yields broadband characteristics and high sensitivity. Correspondingly, it was found that frequencies ranging from a few MHZ (or hundreds of KHz) to several tens or hundred MHz (for example 50 Mhz or 200 MHz) contain important frequencies for imaging the epithelium and sub-epithelial structures. This implies that the use of broad frequency components improves the imaging performance as it recovers more tissue features, over using narrower bands. The exact selection of a bandwidth can be ultimately determined by the physical capabilities of the transducer employed and the desired features to be imaged.

The utilization of frequencies in image formation is likewise a preferred aspect in the invention. In particular, it was found that separation of frequencies in different bands, using appropriate filters applied on the raw signals, is advantageously improving the imaging performance. Images reconstructed at different frequency bands contain different spatial frequencies, i.e different tissue features. Combination of images at different frequency bands can then result in better separation of these features in the combined (composite) image. This is because these different features can be rendered with different intensities or different colors or other rendering scheme to better outline their presence. Another reason is the lower noise power available to narrower band-pass filtered signals, compared to non-filtered or wider band-pass filtered signals. This frequency-band-dependent imaging is also an essential feature of the technique scalability. An alternative utilization of the frequency bands regards the use of a particular frequency per resolution and depth setting desired. For example a different frequency band (higher frequency) is appropriate for imaging the skin epidermis (more superficial structures/higher resolution) vs a lower frequency band for imaging the dermis or hypodermis (deeper seated structures/lower resolution).

An additional preferred aspect of the invention is that the transducer employed collects sound with high acceptance angle. CMUT transducers optimize the angular sensitivity by utilizing material sensitive both to broadband responses and to wide acceptance angle. By making these transducers smaller (order of 100 microns or less) and with thinner membranes it is possible to achieve better detection characteristics and higher angular detection, while fulfilling the design criterion of a pinhole, by reducing their physical size dimensions. For piezoelectric and other sound sensitive material implementation an important feature is the location of the focal point, i.e. the point implementing the virtual pinhole. Typically such points are implemented by imparting curvature in the sound sensitive surface and/or by using acoustic lenses. Focal points can also be achieved by an array of elements, effectively implementing an aperture leading to a pinhole with synthetic methods. In all these cases, a particularly preferred inventive feature herein is associated with the location of the focal point in relation to the medium and the sound detecting surface of the transducer. In particular, it is possible to increase and/or maximize the acceptance angle of the detector and/or pinhole by placing the focal point as close as possible to the sound detecting surface of the transducer (for flat surfaces, typically consisting of multiple elements) or on or close to the virtual surface that passes through the boundary defining the outer border of the curved surface. This is a particularly advantageous preferred feature of the invention, by which the acceptance angle of the pinhole is modulated by the placement of the focal point. This is compatible with other embodiments of the invention herein, whereby the focal point is preferentially located outside the object imaged. Therefore by designing the system whereby the focal point maximizes the acceptance angle by being placed close to the detector, and the overall detector is then placed in proximity to the surface provides an advantageous feature herein. For example, by using a detector having a half-sphere curvature, the focal point is then placed at the center of the surface passing through the boundary of the half sphere, effectively accepting signals through the focal point over virtually 180 degrees. By adapting the exact shape and pinhole placement in this case, the focal point could be placed outside the half sphere, effectively modulating the acceptance angle.

In a preferred implementation, the detection unit comprises at least one deflection element for deflecting the focus points of the detection elements such that the focus points can be positioned at different lateral locations outside of the region of interest, in particular on or above a surface of the object. This allows for an efficient examination of the object without the need of laterally moving the device over the object's surface. The deflection element can be transparent for at least a part of the electromagnetic radiation, which is irradiated by the irradiation unit. In this way, object illumination from the top is enabled. Moreover, integration with other imaging modalities is possible, such as visual inspection through an eyepiece, lens, photography, optical coherence tomography or other microscopy method and with optical resolution optoacoustic imaging. All in all, straightforward illumination and implementation of hybrid imaging approaches are facilitated.

Preferably, the detection unit comprises one or more point-like apertures, which said acoustic waves can pass through. More preferably, the point-like apertures are located in a manner that the major part, preferably more than 70%, more preferably more than 90%, more preferably more than 95%, most preferably more than 99%, of the intensity of the acoustic wave that is to be detected can pass through the point-like apertures before it is detected. The term "aperture" within the meaning of the present invention relates to any means that can be passed through by waves, such as acoustic waves, which are generated in the region of interest of the object upon irradiation with the electromagnetic radiation. The term "point-like", which refers to the term "aperture" within the meaning of the present invention, relates to a small-sized aperture, the size of which is in the range, in particular in the same order, of the desired and/or achievable spatial resolution of the image to be obtained. By this means, the spatial certainty in the obtained images is enhanced without considerable intensity losses. Similarly, the term pin-hole is used to indicate a small aperture.

Preferably, the device comprises an image processing device, which is arranged for processing the light signals and/or the acoustic signals and for generating an optoacoustic image of the object in two or three dimensions. The image is preferably generated using a tomographic reconstruction, which is based on a forward model that encompasses aspects of sound propagation in tissue and aspects of the at least one detector sensitivity field.

Preferably, the device is a handheld device that is adapted for being grasped and held with fingers and/or a hand in order to position the device onto an object under investigation and/or to move the device by hand relative to the object under investigation, in particular by positioning it onto or moving it along an exterior surface of the object. In this way, one can ensure that all body parts in a physician's office or an out-patient examination can be accessed efficiently. The term "handheld device" also relates to optoacoustic imaging devices in which only a component thereof, in particular the irradiation unit and/or the detector unit, is adapted for being grasped and held with fingers and/or a hand for same purposes. Preferably, the size of a handheld device or a respective handheld probe within the meaning of the invention is less than 15 cm in width and/or depth and/or height. The term "handheld device" may further relate to any optoacoustic imaging device which is designed for acquiring tomographic optoacoustic images at arbitrary orientations of the handheld device or handheld probe, respectively. For example, when images from the object are acquired, the orientation of the handheld device or probe can vary from a vertical up to a vertical down orientation and can include all orientations in between, in particular a horizontal orientation.

Hereinafter, further additional or alternative aspects of the invention and preferred or alternative aspects of the invention are elucidated.

According to an additional or alternative aspect of the invention, an optoacoustic device, also referred to as "mesoscopic imaging device", is configured for imaging an object under investigation, in particular a biological object, in a reflectance mode. The term "reflectance mode" refers to placing both the excitation and the detection machinery on the same side of the tissue which is to be imaged. The mesoscopic imaging device includes an optical illumination device, which has a light source device. The light source device, like a pulse laser source or light of modulated intensity and/or modulated phase, is adapted for illuminating the object. To this end, the light source device may include optical reflective and/or refractive components, metamaterials, and/or diffusive components, like mirrors, galvanometers, diffusers, or other moving parts and systems of lenses and of optical filters.

The detector device preferably comprises an acoustic detector device with at least one ultrasonic detector element (transducer), being arranged for collecting acoustic signals, which are created in the object in response to the illumination of the object. The acoustic detector device is arranged so that it allows, i.e. it does not adversely affect, the optical illumination of the tissue. Correspondingly, the optical illumination device is arranged to allow, i.e. not to adversely affect, acoustic (ultrasound) detection from the tissue.

The at least one ultrasound detector is preferably arranged to detect sound passing through a small aperture, also referred to as pinhole. The small aperture is important to enable spatial certainty in the images, which are generated. The detection process from the small aperture can then be modelled assuming a known sensitivity field for the small aperture. The sensitivity field describes the spatial distribution of the relative strength and/or dispersion by which an acoustic source in the tissue is detected by the at least one detector. Image formation is then based on a tomographic approach which can model or approximate the sound propagation and possibly include the particular characteristics of the detector used (for example frequency response and/or he frequency dependent spatial response of the detector system), followed by at least one inversion step to produce the image from the data measured.

Furthermore, the mesoscopic imaging device includes an image processing device, which is arranged for processing the light signals and the acoustic signals and to generate an optoacoustic image of the object in two or three dimensions. The image can be generated using a tomographic reconstruction, which is based on a forward model that encompasses aspects of sound propagation in tissue and aspects of the at least one detector sensitivity field.

It is another additional or alternative aspect of the invention to provide a second detector device, which comprises a light detector device, like an eyepiece, an array of photodetectors, a CCD detector, an optical coherence tomography detector etc., which is arranged for collecting light signals. These light signals are created in the object after an input of the illumination light has been received. Thus, the light detector device, which may include spectrally filtering components, can be adapted for collecting e.g. scattering, reflection, absorption and/or fluorescence image data. The data can be collected with a lens, for example a photographic lens or one of varying magnification. The optical data are generated in response to a second illumination device. Said second illumination device can be identical to the first illumination device, which is used for the creation of optoacoustic images or which could be adapted to the specifics of an optical image. For example, the second illumination device can be an excitation light for the generation of a fluorescence image or a scanned coherent beam, which is part of an optical coherence tomography imaging system. The optical image is helpful to guide the device placement on top of a suspicious lesion. If not with an eyepiece, the device projects the light images on a screen for guiding accurate placement, but also for diagnostic and theranostic purposes. Fiduciary markers can also be used for device placement, either in conjunction with the optical system or independently. Markers that track (on the skin or on the optical image) the field of view of the optoacoustic device for accurate placement would be important. These can be cross-hairs, crosses, dots or other markers, which are projected on the skin or on the optical image from an optical illuminator. The optical image can be used for diagnostic or theranostic imaging or to create a hybrid image on the basis of optical image data and optoacoustic image data reconstructed from the light signals and the acoustic signals.

In this context, the skin/endothelium imaging device, in particular the image processing device is configured for creating optoacoustic images, optical images and hybrid images. The optoacoustic images attain the resolution and overall imaging characteristics of the ultrasound spatial resolution determined by the characteristics of the acoustic detector device and the processing method, which is employed.

Correspondingly, the optical image characteristics depend primarily on the optical detector, which is used and they will vary depending on, whether a CCD detector or another detector, for example an OCT detector is used. In the case of using OCT, three-dimensional views can be considered. However, the spatial resolution of hybrid images may be a combination of features that are available to the different imaging devices and signals, which are collected and can depend on the characteristics, element size and geometry of both optical and acoustic devices.

Therefore, the hybrid image can be a simple superposition of ultrasound and optical images. Alternatively, it could be based on a more elaborate processing scheme that uses features from both systems in order to create a third image.

It is another additional or alternative aspect of the invention to integrate a laser scanning system, which scans the object of interest with a laser beam. An appropriate illumination system can use parts of the machinery of the illumination systems that is described above and/or add components that modify the laser beam, for example by adjusting its width and imparting focusing characteristics. Detection of optoacoustic signals, which are generated in response to this system, can be similarly detected with the ultrasonic transducer present in the system or a second transducer with detection characteristics that are closer to the frequency content generated by the focused laser beam. The system and image formation can also be performed by an image processing device. Said image processing device is arranged for processing the acoustic signals and generating an optical resolution optoacoustic image of the object, which can be used alone or in association with the other images and signals collected in order to form hybrid images.

It is yet another additional or alternative aspect of the invention to generate images, which comprise a variation in resolution and depth by adapting the characteristics of the ultrasound detection, such as frequency or field of view (scan pattern and dimensions) to optimally interface to the dimensions of the particular epithelial disease imaged and time allotted to the examination. This dynamic adaptation is enabled as an automated or a user-defined feature, where the user selects the area to be scanned in the operation console. This selection can be guided by the visual inspection of the lesion before the examination with the inventive device or by inspecting the lesion with the second device feature. The second device feature can also be employed to automatically guide the scan parameters by analyzing the dimensions and possibly the optical properties of the underlying lesion and optimally setting the parameters of the mesoscopic optoacoustic and other scans. For example, it can employ image segmentation algorithms to determine the lesion area and boundaries and then form a scan pattern to optimally interface those boundaries or guide optical-resolution optoacoustic microscopy to a certain area on the skin. The adaptation of some of these parameters can also be done by modification of the detector itself (different transducer, addition of a second transducer to expand the operating range of the device), for example by software adaptations (i.e. use of a broadband transducer and then scan parameters or appropriate filter or processing of broadband opto-acoustic data to achieve the proper depth and resolution).

However, adaptation can also occur in relation with other aspects of the invention by which optical resolution of surface-weighted contrast can be gradually exchanged for high-frequency optoacoustic resolution, which will further reduce at large depths or specimen volumes according to ultrasonic diffraction principles. This will result to images, which integrate these scalable imaging characteristics projected for diagnostic and theranostic readings.

Scalability can be granted in particular by employing detector elements with a wide-band ultrasound frequency detection ability. Beneficial performance is achieved for detection in bands as broad as a few hundred KHz to a few hundred MHz. Preferred implementations are carried out using single transducer elements built from Lithium Niobate (LiNbO3) crystal material, constructed in a curved mode to allow wide acceptance angle and detecting from 2 Mhz to 200 MHz. Alternatively, multiple transducers can be used to detect at different frequency bands, for example one transducer covering the 0.5-10 Mhz range and another the 10 Mhz to 50 Mhz range; the exact values given herein only as examples. The transducers could be scanned in parallel placed in proximity to each-other.

The invention does not only significantly improve on penetration depths of optical imaging, using ultrasound broadband detection, but can also adapt the resolution with depth, spanning from specimen of a few hundred microns in depth (diameter) and a few microns resolution to specimen of approx. 5 mm in diameter and less than 30 μm resolution by adapting the frequency range employed from broad-band transducers or even utilizing different acoustic sensors for the different frequencies to be considered.

This approach can be employed to combine many diverse features from the signals collected and capitalize on diverse optical contrast parameters, including imaging of intrinsic contrast (lesion boundaries, blood vessels, oxygenated and deoxygenated hemoglobin, melanin, various metabolites, oxygenation or hypoxia) or extrinsically administered agents, such as optical dyes, fluorochromes or nanoparticles. Detection of these biomarkers can be achieved at a single wavelength or after multi-wavelength illumination of the tissue, collection of images at different wavelengths and the spectral processing of these images to identify certain absorption signatures of the underlying moieties of interest.

The device can operate using multi-spectral optoacoustic tomography (MSOT) principles, by utilizing illumination at multiple wavelengths and spectral processing methods to retrieve anatomical, functional/physiological and molecular parameters in-vivo. Biomarkers can also be resolved as time signatures, where variations of absorbing parameters over time can be instead recorded to identify structural, physiological or even molecular features in the tissue. This can be achieved by taking differences between images or more generally match the images to certain dynamic patterns revealing specific tissue characteristics.

According to a preferred aspect of the invention an acoustic detector is used, which is arranged to detect sound from a pinhole. This can be achieved for example by focused electro-acoustic transducers, such as piezoelectric transducers (PZT), which detect signals only from a small aperture, using capacitive transducers CMUT (Capacitive micromachined ultrasonic transducers), hydrophones or other silicon based transducers. Similarly, detector locations (detector arrays) can be implemented using detector elements based on optical interferometry or silicon photonics. In all these preferred cases, the sound is detected over a grid of small apertures (pin-hole) and is considered unfocused, i.e. it detects light from multiple diverse acceptance angles (projections). By use of the effective surface (intermediate surface) the grid of pinholes is at an invariable distance from the object imaged, which is a particularly preferred feature in the invention herein, to ensure that the pinhole grid (point-like detection locations) has an invariable distance from the object or the surface of the object imaged throughout the data collection process. In this manner, even detector scanning implementations, for example for implementations/devices using a single or a small number of detectors to establish a pin-hole grid, can yield high resolution imaging in handheld operation, despite the possible user-dependent movement. This arrangement is also preferred even for stationary scanners, to prevent against object movement. For example if the object is the arm of a person, the establishment of the effective surface aids in avoiding the translation of the person's movement to breaking the condition of invariable distance and resulting in motion artifacts and resolution deterioration. These signals, generated under conditions of an invariable distance are then tomographically reconstructed to reveal a two or three-dimensional image.

Such "pinhole" apertures can be implemented in different ways. One way is to implement the aperture physically using detectors of small size, for example CMUT based detectors, silicon/silica detectors or physically small interferometric detectors, and for example fiber based detectors. An important technology herein is silicon photonics, whereby sound is similarly detected from a small physical area. Another way is to implement the aperture geometrically and electronically using elements of curved surfaces and/or acoustic lenses, so as to preferentially detect from a small focal point and/or by employing timing to further control the detection characteristics, for example by a delay and sum technique. In this case, a set of moving stages, an acoustic and/or optical mirror or a combination of moving stages and mirrors may be used to establish a detector pattern onto the area. Still another way is to implement a pinhole utilizing an interferometry fiber, such as fibers incorporating Bragg gratings or Fabry-Perot resonators. It may be an alternative to enclose the detector using a material and allowing only a small opening, by which sound can reach the detector. To achieve such an implementation, a sound reflecting material or a sound absorbing material or a combination of the two materials is positioned to enclose the detector and allow access to the detector from sound waves, which only pass through the small physical opening. Typically, liquid-air interfaces can nicely achieve sound reflection, for example a hollow glass surface. To avoid reflections, padding with sound absorbing material (or void structures not propagating sound) would be necessary or the enlargement of the physical pinhole to reduce the sound interference with the walls of the detector protection. It is helpful in this detection approach to surround the detector (besides the opening) with a sound absorbing material to prevent reflected sound from re-entering the medium. Alternatively, if efficient sound absorption can be ensured by the surrounding of the medium (except the open aperture, i.e. pinhole), the reflecting material can be avoided altogether.

A potent alternative is the use of a point detector from a material that transmits sound (for example a metal hairpin or needle) surrounded by a material that does not transmit or establishes high sound reflection sound, for example void or air. By scanning the needle one can take pinhole measurements from multiple points. A system with multiple needles can also be foreseen, in order to parallelize the detection. The needles can be directed to multiple sensors read in parallel.

The transducers mentioned above preferably comprise electro-transducers, i.e. piezoelectric, capacitive or silicon transducers. Silicon transducers include wafer-based transducers or interferometric fiber based transducers, which also allow illumination through them. The use of a laser beam scanning and detecting via the use of an interferometer is a preferred approach herein, implemented by means of the effective surface. However, the use of piezoelectric detectors or cMUT's can lead to even more preferred approaches, especially for allowing parallel detection, or when they can achieved more broadband detection and smaller/more lightweight implementations compared to interferometric detectors. Therefore, for further reducing the width, size and costs and increasing the portability, the use of electro-acoustic detectors (CMUT, silicon, fiber, and physical pinhole) would be preferred.

Preferably, the pinhole detector elements are located along a predetermined reference surface, for example a flat surface, convex or concave surface and are coupled to tissue through a medium that couples acoustic energy. The medium can further disperse light. The medium dispersion is useful for homogeneously distributing illumination light to the tissue surface. The medium could also be a layered medium that disperses light in a circular manner to illuminate tissue in a ring pattern. The medium could be a unit that establishes the effective surface, could be part of the effective surface, be in contact with the effective surface or be delineated at least in one side by the effective surface.

Preferably, the detectors in operation have a focus point that is placed outside of the tissue, for example 0.1-10 mm away from the tissue surface. Sound captured in this mode comes from multiple diverse points within the medium, but collected through a virtual small spatial aperture, which yields spatial certainty, but angle uncertainty, as to the origin of data. However, using multiple points arranged in a two-dimensional grid, these data can then be converted to high resolution images using previously described tomographic approaches, such as back-projection or model based approaches. As outlined, a pinhole in proximity to the active detection surface of the detector increases the acceptance angle of the pinhole and leads to an increased number of projections available for tomography. This design improves the image reconstruction and image performance.

In another additional or alternative aspect of the invention, a focused ultrasound detector, for example an electro-acoustic ultrasound detector, scans the detector or focal point to establish the pattern of small aperture detection. Effectively, the focal area of the transducer is considered an unfocused small aperture detector. Herein, the aperture is established electronically using the curved shape of the detector and adding of delayed signals to detect signals that come from lines passing within the detector aperture. Measures to account for sound diffraction and overall the finite-area of the detector may be further necessary to enable accurate detection, since these detectors tend to have large detection area, therefore not itself establishing a pinhole, but only by means of electronic processing and/or mathematical modelling of the exact detection ability of the transducer's area. Modelling of the detection also offers measuring to account for the particular acceptance characteristics. These models can be incorporated in a forward model describing the sound propagation and detection and then subsequent mathematical inversion, which establishes pinhole operation by means of incorporating the detector model in the forward problem.

Another preferred feature of the device relates to illumination methods appropriate for interfacing light onto tissue. The illumination implementations considered are advantageous for the operation of the scanner. Illumination herein is administered preferably as surface illumination provided either by trans-illuminating, also referred to as front illumination, through the pattern of point detectors using plane wave illumination or patterned illumination, for example ring illumination. This can, for example, be achieved through a surface which deflects sound emitted from tissue to the system but allows light to pass through the surface at the wavelength of interest. Trans-illumination can also be achieved through an appropriately modified chip of capacitive transducers or interferometric transducers, assuming the wafer or surface is appropriately treated to pass light, as a meta-material. A diffuser can be also used to make the illumination more homogeneous, at any illumination pattern (ring, rectangular etc) and either used in trans-illumination mode or placed under the line of detectors. For example, a diffuser could be implemented as a volume enclosed within surfaces and containing a scattering medium (for example a liquid scatterer, a gel scatterer such as Agar and $TiO_2$ spheres or intralipid, or a solid scatterer with appropriate acoustic propagation properties). The enclosing surface may be a light reflecting surface. Light can be injected in the scattering volume through an optical guide from one or multiple locations. Injected light is scattered around and reflected by the enclosing surfaces. Obviously the surface that comes in contact with tissue is not reflecting, and therefore allows the deposition of all photons in the tissue. In that respect, a homogenous photon pattern is injected from a ring or from a rectangle into the tissue to excite optoacoustic responses. More common alternatives include directly injecting light into tissue by bringing optical fibers in close proximity or direct contact with tissue. An advantage of the enclosed surface is that a distributed illumination pattern can be achieved. While in principle homogeneous illumination is preferred, ring, donut or rectangular illumination where the center is not strongly illuminated (rectangular donut) are preferred to improve dynamic range considerations, stemming from depositing high amounts of light energy directly in front of the pinhole. In this case, adjusting the light energy away from the transducer can improve visibility and dynamic range.

Moreover, the invention preferably relates to the use of light illumination of one time-varying parameter in the form of amplitude, frequency or phase. When amplitude variations are considered, these can be in the form of ultra-short light pulses such as the ones coming from Ti:Saphire lasers, Optical Parametric Oscillators or laser diodes, light emitting diodes, fiber lasers or other light producing elements. Alternatively, varying amplitude can also be established via the use of intensity modulated lasers and laser diodes. Finally, frequency or phase modulated light sources can be also considered. Details of implementing frequency domain imaging have been established in published patent application WO 2013/167147 A1, which is incorporated herein by reference.

As a further advantage of the invention, the light source device of a hybrid opto-acoustic mesoscope device can be adapted for various illumination types, like a wide-field illumination, a patterned illumination, a single plane illumination, a focused illumination and/or a pencil-beam illumination of the object. With the wide-field illumination, a surface region of the object covering a region of investigation is homogeneously illuminated. Correspondingly, the patterned or the focused illumination yields a patterned or focused light field distribution on the surface region of the object; which can be time-varying, e.g. by scanning the pattern or light focus. More than one illumination types can be combined, depending on the particular imaging performance characteristics required. The direction of the illumination can be established from one side of the object, in particular when imaging epithelial tissues whereby access to the tissue is only possible from one side of the tissue.

Preferably, direction of the illumination for the primary device features, i.e. the acoustic resolution mesoscopy, can occur in two major ways. One is through the optical and acoustic system by using transparent components or meta-materials. The second is laterally by coupling light from the sides of the field of view, typically using an expanding system, a reflective and/or diffusive medium to homogeneously distribute light in the tissue. For example, the coupling medium of a detector to the tissue could be a diffusive gel or fluid, containing multiple scatterers such as lipids, $TiO_2$ particles or other scattering media. The fluid could be enclosed by a reflective surface, such as a mirror or reflecting foil, such as a white foil or silver or aluminum foil to reflect photons escaping the coupling gel back into the coupling medium and tissue. Both ways of illumination can be combined.

According to yet another alternative embodiment, an acoustic transparent mirror is utilized which reflects sound to a single element detector but are scanned using galvo-based devices or other fast motor-stages in order to offer the equivalent raster scan of using a two dimensional acoustic detector grid pattern. Although not as fast as a CMUT-based system, using a single detector and an acoustic scanned mirror combination has the advantage of a transparent sound deflecting device which allows for an implementation of additional imaging modes. The use of an optically transparent mirror in this case can facilitate object Illumination from the top and integration with other imaging modalities such as visual inspection through an eyepiece (which is a preferred embodiment), lens, photography, optical coherence tomography or other microscopy method and with optical resolution opto-acoustic imaging. This contributes to a practical system and it is particularly attractive to facilitate straightforward illumination and to implement hybrid imaging approached.

According to another particularly preferred embodiment of the invention, the image processing device is configured for creating not only optoacoustic mesoscope images, but further at least one of an optical image and/or an optical resolution opto-acoustic image. In particular, the optical image has the advantage that the arrangement of the acoustic detector device can be done under optical control, i.e. the acoustic detector device can be positioned relative to the object in dependency on optical image data collected with the object. The optical image can be also used for conventional tissue and lesion inspection for diagnostic or theranostic purposes in analogy to the current practice in dermatology. However, as already indicated, the optical image can also imply a tomographic optical image, for example an optical coherence tomography image offering high resolution three-dimensional images of the first few hundred microns to millimetres of tissue and the acoustic resolution imaging revealing co-registered contrast also extending deeper in tissue. As a further advantage, the optical image data and/or the opto-acoustic image data can be used for reconstructing the opto-acoustic image and the optical image, resp., and vice versa.

Generally, the object to be imaged may comprise e.g. human skin, animal skin or other superficial tissue up to several millimetres. Different levels of miniaturized technology are considered so that the present inventive approach can be also added to endoscopic devices so that it can image internal epithelial disease including colon, oesophagus or the linings of internal organs and vessels. In the latter case, the light source device, the light detector device and the acoustic detector device are coupled with into the endoscope device. Preferably, the acoustic detector device is arranged on a distal portion of the endoscope device, so that hybrid or opto-acoustic images can be collected representing an inner portion of the object investigated.

The above and other elements, features, steps, characteristics and advantages of the present invention will be more apparent from the following detailed description of preferred embodiments with reference to the following figures:

FIG. 1 shows a cross-sectional view of an embodiment of a device for opto-acoustic imaging;

FIGS. 2 a) and b) show cross-sectional views of two further preferred embodiments of a device for optoacoustic imaging;

FIGS. 3 a) to d) show cross-sectional views of preferred embodiments of detection units for detecting acoustic signals;

FIGS. 4 a) to c) show perspective views of preferred embodiments of a device for optoacoustic imaging using rotating deflection elements and/or rotating detection elements;

FIG. 5 shows a side view of a preferred embodiment for fast rotational motion of a deflection element;

FIG. 6 shows different views of a preferred embodiment of a deflection element surrounded by a matching material;

Figure 1:
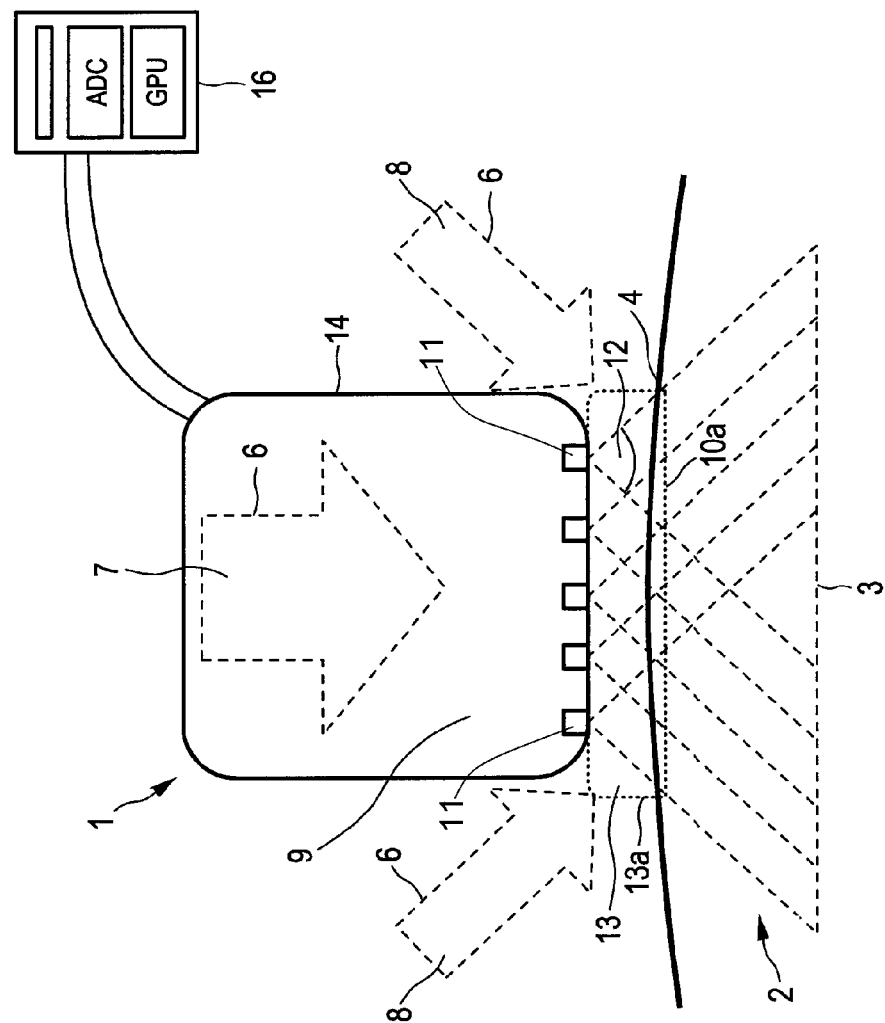

FIG. 1 shows a cross-sectional view of an embodiment of a device 1 for opto-acoustic imaging of a region of interest 3 of a tissue 2. The region of interest 3 is irradiated with electromagnetic radiation 6 generated by an irradiation unit (not shown) via illuminating the surface 4 of the tissue 2, either in front illumination 7, also referred to as trans-illumination, or in side illumination 8 or in a combination of front illumination 7 and side illumination 8.

The irradiation unit may comprise pulsed lasers, such as Ti:Saphire lasers, light guides, microwave pulses, laser diodes, light emitting diodes, fiber lasers and other elements that are configured to provide a pulsed illumination of the tissue 4. Moreover, the irradiation unit may include one or more laser scanning systems and/or interferometers. In addition, the electromagnetic radiation 6 may exhibit a modulated intensity and/or a modulated phase and/or an adjustable beam width. Alternatively, the irradiation unit can comprise an electric generator, which is configured to generate pulsed heat in the tissue 2 in order to achieve thermoacoustic images.

Furthermore, the device 1 comprises an enclosure 14, preferably of a size that is appropriate for hand-held use, which encloses a detection pattern 9 for detecting acoustic waves, which are generated in the region of interest 3 of the tissue 2 upon irradiation with electromagnetic radiation 6. The detection pattern 9 comprises several point-like detection positions 11, also referred to as point-like detector elements, which can be implemented using at least one of piezoelectric transducers (PZT), capacitive transducers, preferably capacitive micro-machined ultrasound transducers (CMUT), hydrophones, silicon based transducers and optical interferometry-based sound detectors, such as fiber Bragg-based detectors or Fabry-Perot based detectors. The term element implies herein a pinhole, i.e. a point whereby sound arrives from multiple directions and is detected, not necessarily a physical detection element such as a transducer. For example, the element could be a transducer, or the focal point of a transducer located elsewhere. Due to the small size of the point-like detection elements 11, a large portion of the intensity of the front illumination 7 passes the detection pattern 9 and reaches the tissue 2, in particular the region of interest 3 of the tissue 2. Preferably, the side illumination 8 is configured to bypass the point-like detection elements 11 of the detection unit 9.

Preferably, the point-like detection elements 11 are arranged in a one- or two-dimensional array configuration. This configuration could be linear (flat) or curved. It is also preferred that the detection elements 11 are located above the region of interest 3 of the tissue 2, in particular above the surface 4 of the tissue 2. Alternatively, the point-like detection elements 11 can also be located, for example, on the surface 4 of the tissue 2, below the tissue 2 or even inside the tissue 2, i.e. below the surface 4 of the tissue 2.

Preferably, an effective surface 13 is provided as an intermediate surface between the detectors or the point-like detector elements, to establish an invariable distance between the point-like detection elements 11 and the surface 4 of the tissue 2. The effective surface could be a coupling medium of discrete width for optically and/or acoustically coupling tissue 2 and detection unit 9, an infinitely thin membrane or other arrangements establishing an effective surface, which may further contain or enclose a coupling medium. In order to avoid or to reduce reflection losses of the electromagnetic radiation 6 and/or the acoustic waves at the interface in between the surface 4 of the tissue 2 and the coupling medium 13, the coupling medium 13 preferably exhibits a refractive index, which is close or identical to the refractive index of the tissue 2.

In the present example, the device 1 comprises a container 13a in which the coupling medium is provided. The container 13a comprises a bottom wall the outer surface 10a of which is in contact with the object 2 and establishes in this case the effective surface. Consistent with the description above, the coupling medium is considered in this case as part of the handheld sensor. By means of the bottom wall of the container 13a, a pre-defined distance (invariable distance) is maintained between the surface 4 of the object 2 and/or the region of interest 3 within the object 2 on the one hand and the point-like detection elements 11 on the other hand. Preferably, the outer surface 10a, which is also referred to as intermediate surface 10a, is arranged and/or designed for maintaining the object 2 in a stable position relative to the intermediate surface 10a, preferably such that the object 2 cannot be readily moved in relation to the intermediate surface 10a during the optoacoustic imaging of the object 2, for example that any movement of the object or the device is concurrently translated to the device or the object respectively The point-like detection elements 11 are configured to detect acoustic waves emanating from the region of interest 3 within a given field of view 12, also referred to as acceptance angle, i.e. a solid angle within which the respective detection element 11 is sensitive to acoustic waves.

The detection unit 9 and preferably also the irradiation unit are integrated in a casing 14 which may be filled with a wave-propagating medium, which can be liquid, solid, gaseous, jellylike or foamy.

The optoacoustic imaging device 1 further comprises a processing device 16 for processing the detector signals generated by the detecting elements 11 and for reconstructing images based on the processed detector signals. For example, the processing device 16 comprises an analog-to-digital converter (ADC) for converting analog detector signals of the detecting elements 11 to corresponding digital detector signals and a graphic processing unit (GPU). In the example shown, the processing device 16 is arranged separately from the casing 14. However, in an alternative configuration (not shown), the processing device 16 can also be integrated in the casing 14.

FIG. 2 a) and b) show cross-sectional views of two further preferred embodiments of a device 1 for optoacoustic imaging. In distinction to the embodiment shown in FIG. 1, where point-like detection locations are given by point-like sound detection elements 11, in the embodiments of FIG. 2 the point-like detection locations are given by point-like focus points 19 of sound detection elements 23. The focus points 19 and the detection elements 23 are part of detection unit 9.

Figure 2A:
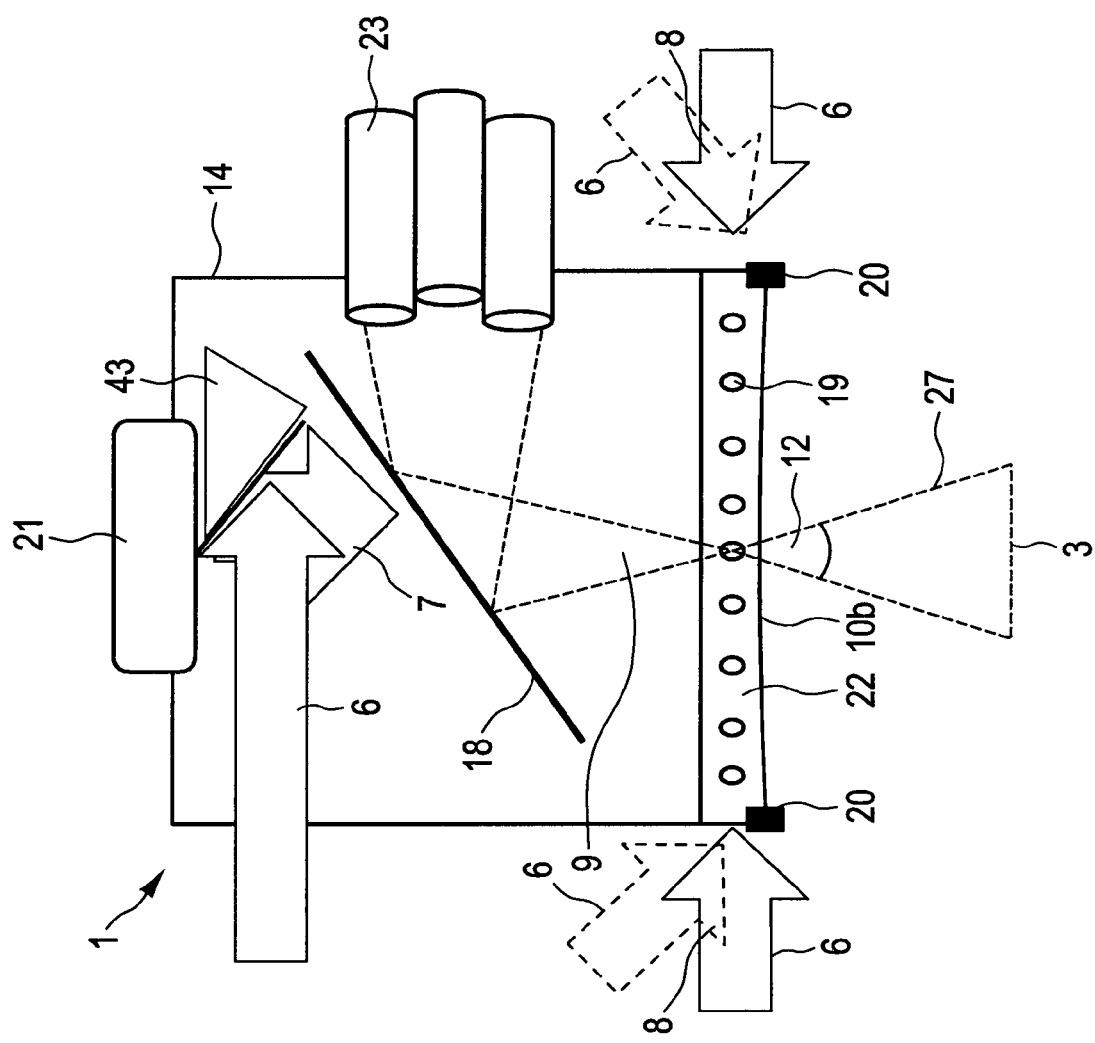

In the example given in FIG. 2a a front illumination 7 and/or a side illumination 8 setup is provided for irradiating the region of interest 3 of the tissue with electromagnetic radiation 6. Preferably, the front illumination 7 is provided by deflecting electromagnetic radiation 6 at a deflecting element 43 towards the region of interest 3 of the tissue. Regarding the side illumination 8, the elucidations in connection with the example given in FIG. 1 apply accordingly.

In the given example, a plurality of focus points 19 are provided, which are preferably arranged in a one- or two-dimensional array 22. Each focus point 19 has a field of view 12, which is suited for collecting acoustic waves that are generated in the region of interest 3 of the tissue.

The focus points 19 correspond to respective focal points of focused sound detection elements 23, as exemplarily indicated for one focus point 19 by dashed lines. Preferably, an acoustic deflection element 18 is provided for deflecting sound waves emanating from the region of interest 3 and passing through the focus points 19 to the detection elements 23. Preferably, the detection elements 23 are located outside the path of the front illumination 7, while the acoustic deflection element 18 may be located in said path of the front illumination 7.

Accordingly, the acoustic deflection element 18 is preferably transparent for the electromagnetic radiation 6 of the front illumination 7. Alternatively or additionally, the acoustic deflection element 18 may deflect or refract the electromagnetic radiation 6 of the front illumination 7. The detection elements 23 can be provided outside the casing 14 or inside or partially inside the casing 14.

Figure 9:
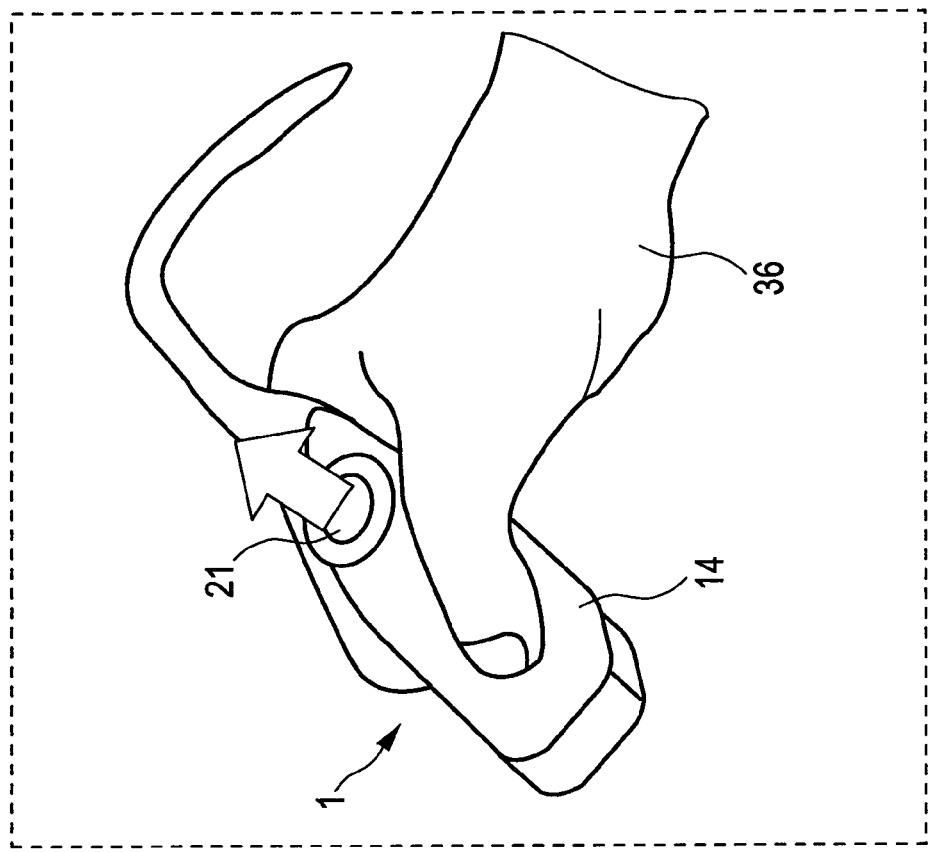
FIG. 9 shows a perspective view of a preferred embodiment of a device for optoacoustic imaging, which is provided for handheld applications.

Preferably, a port 21, in particular an optical port, may be provided for visual inspection of the tissue under investigation. Visual inspection occurs preferably in an optical manner, e.g. by using an eyepiece, a camera or similar. This is illustrated in FIG. 9, which shows a perspective view of a preferred embodiment of a device 1 for optoacoustic imaging, which is designed for handheld applications. In this case, at least the major part of the components for illuminating the region of interest 3 of the tissue and detecting acoustic waves generated in said region of interest 3 of the tissue upon irradiation, are housed in casing 14, which is configured to be held in the hand 39 of a user, who can examine the tissue by moving the device 1 onto the surface of the tissue. Alternatively, the device 1 may also be held by a user in an indirect manner, which can for example be realized by an additional handle or any other holder that may be attached to the casing 14 and directly held by the user's hand 39. At a top portion of the casing 14 of the handheld device 1, an eyepiece and/or an optical imaging port 21 is provided, which allows for a direct visual inspection of the investigated tissue and/or for a transfer of optical images to any processing and/or display device configured to process and/or display optical images of the tissue.

Furthermore, the bottom part of the device 1 according to FIG. 2a may comprise a bottom wall, e.g. of plastic, metal or other material, that is fixed by a rim 20 in order to enclose the coupling medium 13 forming an interface to the tissue 2. The rim 20 can further act in a bottom wall straightening or tightening manner, whereby a slight pressure of the device 1 onto the tissues 2 can cause an ex-tension of the tissue 2 in order to provide a more flat surface and minimize folds and wrinkles.

Similarly to the example given in FIG. 1, the bottom wall of the bottom part of the device 1 shown in FIG. 2 has an outer surface 10b by means of which a pre-defined distance between the surface of the object and/or the region of interest 3 within the object and the point-like detection elements, i.e. the focus points 19, can be easily and reliably maintained during image acquisition. The outer surface 10b, which is also referred to as intermediate surface 10b, is arranged and/or designed for maintaining the object in a stable position relative to the intermediate surface 10b.

Figure 2B:
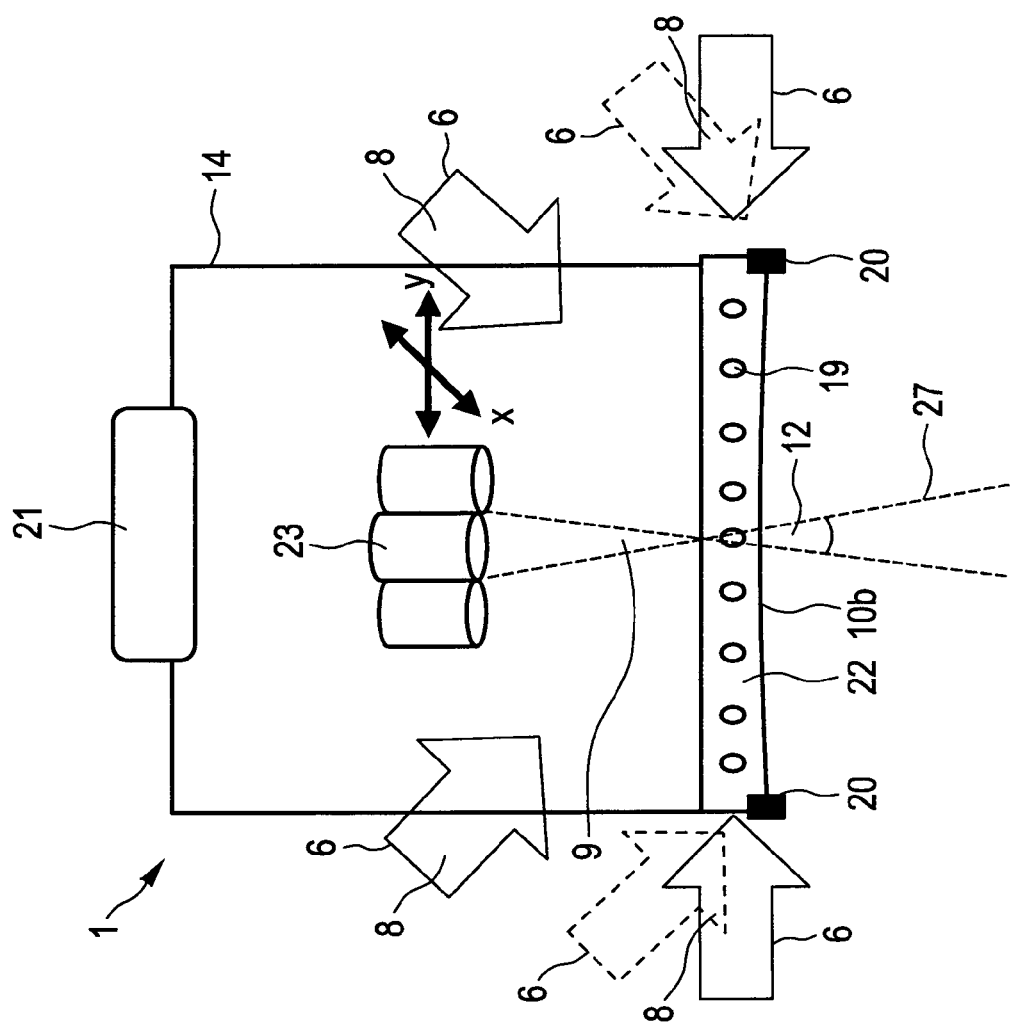

FIG. 2b shows a preferred alternative of the embodiment shown in FIG. 2a. In this alternative embodiment, the detection elements 23 are located inside the enclosure 14 and are translated along a two- or three-dimensional pattern, correspondingly establishing a pinhole pattern. In this way, acoustic waves, which are generated in the region of interest 3 of the tissue and which passed through the focus points 19, can be collected directly. In this context, the term "directly" means that no additional acoustic component such as an acoustic deflection element 18 shown in FIG. 2a is necessary to collect acoustic waves. This may consequently lead to a more compact design of the device. However, no front illumination 7 (see FIG. 2a) is provided in this case, because the detection elements 23 may adversely affect the propagation of electromagnetic radiation 6. Accordingly, instead of front illumination 7 side illumination 8 is preferred. Regarding the side illumination 8 and other aspects of the device 1, the elucidations in connection with the example given in FIG. 1 apply accordingly. Regarding the outer surface 10b of the bottom wall of the bottom part of the device 1 the above elucidations relating to FIG. 2a apply accordingly.

A particularly preferred embodiment of the invention is based on the implementation of FIG. 2b. At least one piezoelectric transducer is enclosed into the enclosure 14 and scanned with a two-dimensional miniaturized translation stage to establish a two-dimensional grid of pinholes, one of these pinhole locations are exemplified by pinhole 19. The pinhole in this case is established as the focus point of the transducer, i.e. the pinhole is not the piezoelectric surface itself, but the focal point established by the piezoelectric surface. This focal point can be established using a curved piezoelectric surface, as shown in FIG. 3c, which will be elucidated in more detail below. Acoustic lenses could be additionally or alternatively used. A preferred aspect of the transducer is that the focal point is not established away from the curved surface, as schematically shown in FIG. 2 and FIG. 3c, but very close to the transducer, preferably close to the center of the disk (flat surface) established by the border of the curved surface of the transducer shown on FIG. 3c. For example the curved surface could be half sphere (180 degrees coverage) or an ellipse or other sphere of similar coverage. By bringing the focal point close to the transducer, a wide acceptance angle 12 is established, for example an acceptance angle larger than 90 degrees, preferably larger than 120 degrees, and can be employed for tomographic mesoscopy. Correspondingly, the entire transducer in FIG. 2b is preferably placed close to the effective surface 10b for example within 1 mm or closer from surface 10b. Surface 10b establishes contact and friction with the surface of the object imaged so as to establish and maintain an invariable distance.

According to another preferred aspect of the device 1, in addition to the effective surface 10b, i.e. the intermediate surface, a rim 20 (the cross-section of which is shown in FIG. 2b) is further employed to establish the invariable distance between the pinhole grid 22 and the object. Since in the preferred implementation in FIG. 2b scanning of the detector or detectors 23 is assumed, the establishment of an invariable distance is particularly advantageous for high-resolution imaging.

The illumination in the embodiment of FIG. 2b can be given by side illumination 8 at an angle, which could be broad-beam or of another profile (not shown), for example structured or adaptive. Side illumination 8 is shown also by alternative implementations just above the effective surface 10b. If only side illumination is employed, it is preferably implied that the medium around the pinhole pattern 22 may contain optically deflecting or scattering matter, surrounded by an optically reflecting surface so as to direct as much of the light energy from side illumination to the object. Finally, transillumination would be also possible in this implementation, in analogy to beam 7 in FIG. 1. A preferred implementation may construct a part of the inside of the enclosure 14 from optically reflective material so as to further establish the enclosure 14 as an illumination unit, in remote analogy to an integrating sphere. In this case, even if the transducer(s) 23 will be interfering with the direct component of light, light energy coupling to the tissue, i.e. the object, would be still possible due to propagating light within the enclosure 14.

FIGS. 3a) to d) show cross-sectional views of preferred embodiments of detection units 9 for detecting acoustic signals, wherein point-like detection locations are given by point-like apertures 42.

In the embodiment shown in FIG. 3a a focused sound detection element 23 configured to collect acoustic waves is provided within a cavity 41 exhibiting a triangular shape. The cavity 42 has wide end, at which the detection element 23 is provided, and a narrow end forming a point-like aperture 42, also referred to as pinhole, by which a field of view 12 of the detection element 23 is defined. Acoustic waves emanating from a tissue under investigation and propagating within the field of view 12 will pass the point-like aperture 42, enter the cavity 41 and be detected by the detection element 23. Preferably, the cavity 41 is formed by ultrasound-opaque, in particular ultrasound reflecting and/or absorbing, elements 24. The detection unit 9 according to FIG. 3a may also comprise an acoustic lens 25 which is designed for focusing acoustic waves to the sensitive area of the detection element 23.

Preferably, at least parts of the lower surfaces 10c of the ultrasound-opaque elements 24 allow for maintaining a pre-defined distance between the surface of the object and/or the region of interest within the object and the point-like detection entity, i.e. the point-like aperture 42. The surfaces 10c are also referred to as intermediate surfaces 10c and are preferably arranged and/or designed for maintaining the object in a stable position relative to the intermediate surface 10c and/or the point-like aperture 42.

In FIG. 3b an alternative embodiment is shown, wherein instead of a cavity 41 (see FIG. 3a) a casing 14 is provided, which is preferably filled with an ultrasonic, wave-propagating medium 28. Preferably, the ultrasonic, wave-propagating medium is 28 is a fluid. Additionally, FIG. 3b shows a wavelength filter 26, which filters out acoustic wavelengths, which shall not be collected and/or detected by the detection element 23. Regarding the detection element 23, ultrasound reflective and/or absorbing elements 24, acoustic lens 25 and point-like aperture as well as the lower surfaces 10d of the ultrasound-opaque elements 24, the above elucidations in connection with FIG. 3a apply accordingly.

FIG. 3c shows another preferred embodiment, where a focused ultrasound detection element 23 is provided with a cone-shaped cap, which is preferably made of a solid ultrasonic wave-propagating medium 28. The tip of the cap constitutes a point-like aperture 42 or pinhole through which sound waves emanating from the tissue pass. Accordingly, no additional sound guiding elements 24 or casing 14 (see FIGS. 3a and 3b) are necessary. As exemplarily shown in FIG. 3d, the cap can also have the shape of a pointed cone.

FIGS. 4 a) to c) show perspective views of preferred alternative embodiments of a device 1 for optoacoustic imaging, wherein at least one point-like detection location in form of a focus point of detection element 23 scans the region of interest of tissue 2. To this purpose, movable, preferably rotating, deflection elements 18 and/or movable, preferably rotating, detection elements 23 are provided.

Figure 4A:
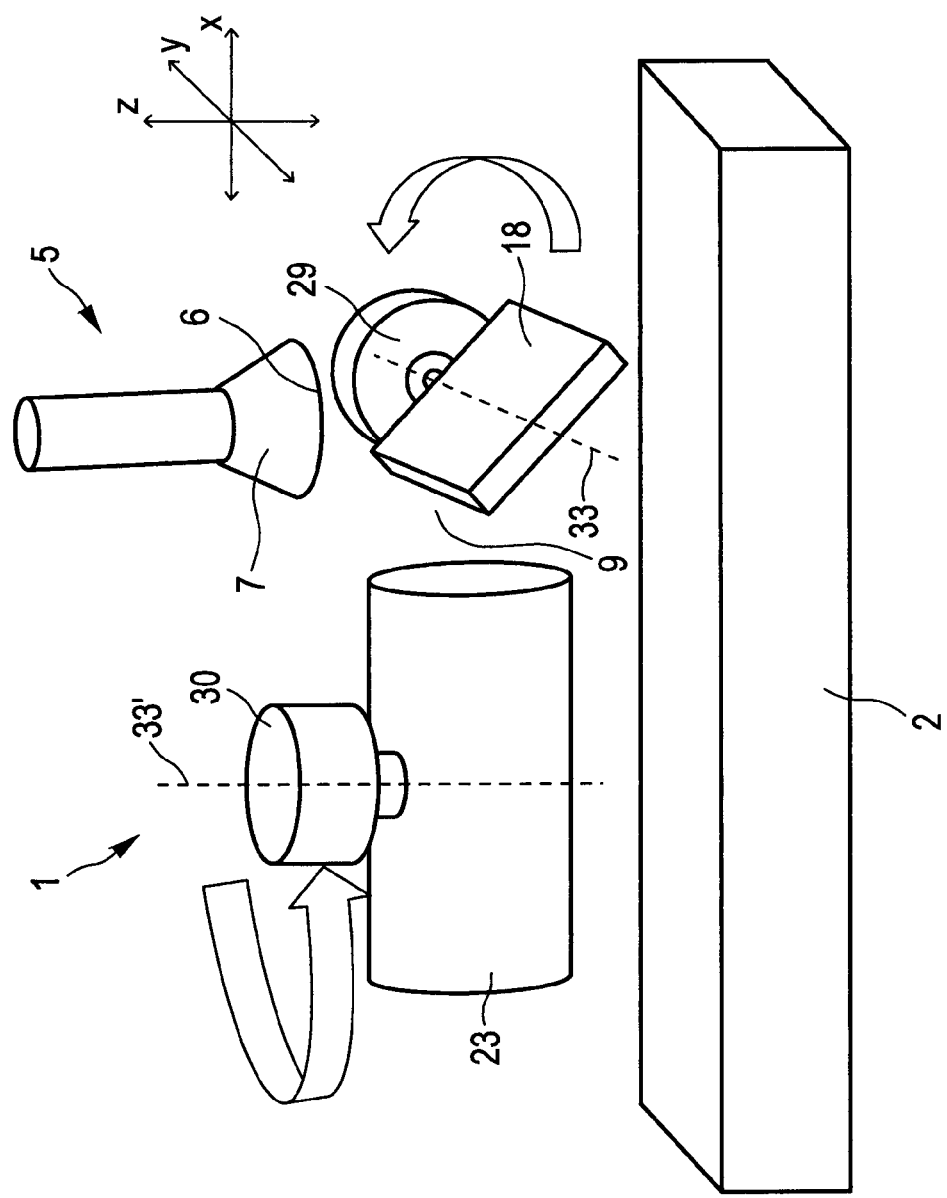

In the example given in FIG. 4a, the optoacoustic imaging device 1 comprises a detection unit 9 for detecting acoustic waves generated in tissue 2. Electromagnetic radiation 6 originating from an irradiation unit 5 irradiates the tissue 2 in front irradiation 7. The detection unit 9 comprises an acoustic deflection element 18 for deflecting acoustic waves emanating from tissue 2 and a detection element 23 for detecting the acoustic waves reflected at the deflection element 18.

Preferably, both the acoustic deflection element 18 and the detection element 23 can be rotated around an axis of rotation 33 and 33', respectively. In the present example, the axis of rotation 33 of deflection element 18 running along y direction is perpendicular to the axis of rotation 33' of detection element 23 running along z direction. By this means, scanning of the focus point of the detection element 23 over tissue 2 is possible along a desired plane and/or direction, e.g. in y direction or in x-y plane.

Regarding the rotation of the acoustic deflection element 18, a deflection element rotator 29 is provided. Regarding the rotation of the detection element 23, a detection element rotator 30 is provided. Preferably, the deflection element rotator 29 and/or the detection element rotator 30 constitute a mechanical device, however, other mechanisms including optical, electronic and magnetic mechanisms can be provided as rotator 29 or 30, respectively.

It should be noted that preferred embodiments of the invention are not limited to the above-mentioned different axis of rotation 33 and 33'. As exemplarily shown in FIG. 4b, a single axis of rotation 33 of the deflection element 18 along the x direction can be provided. The axis of rotation 33 is substantially parallel to the surface of tissue 2 and/or to the orientation and/or symmetry axis of detection element 23. By rotating the deflection element 18 around axis 33, acoustic waves emanating from a, preferably linear, region of interest of tissue 2 along y direction are deflected at the deflection element 18 and detected by detection element 23. Preferably, in order to allow for a scanning of the tissue 2 also in x direction, a translational drive may be provided for moving, in particular translating, the deflection element 18 and/or the detection element 23 parallel to or along rotational axis 33. Regarding the remaining components of the device 1, in particular the irradiation unit 5, the elucidations with reference to FIG. 4a apply accordingly.

In FIG. 4c another preferred embodiment is shown. Detection unit 9 comprises a detection element 23 and two rotating acoustic deflection elements 18. Preferably, respective axis 33 and 33' of rotation of the deflection elements 18 are perpendicular to each other. In the present example, the detection element 23 is cone-shaped, but may have any other shape. Using two rotatable deflection elements 18 allows for scanning the focus point of the detection element 23 over the tissue 2 in the desired plane, e.g. x-y plane, or direction, e.g. z direction, in a simple and compact manner.

FIG. 5 shows a side view of another preferred embodiment for fast rotational motion of an acoustic deflection element 18. Preferably, the detection element 23 for detecting acoustic waves is rotatable around an axis of rotation 33 using an appropriate drive (not shown). The rotational motion of the acoustic deflection element 18 around its axis of rotation 33' is driven by a cam 34 attached to a rotating motor (not shown). Two magnets 35 and 35' are provided, wherein one magnet 35 is provided, in particular fixed, at the acoustic deflection element 18 and the other magnet 35' is fixed in place, e.g. fixed at the device. By means of rotating cam 34, the acoustic reflector 18 (shown here in its initial position) is rotated counterclockwise about a certain angle of rotation. When continuing the counterclockwise rotation of the cam 34, the deflection element 18, after having reached a maximum angle of rotation, is rotated clockwise back to its initial position due to attraction forces caused by the magnets 35 and 35'. Instead of magnets, other elements causing reset forces to the acoustic reflector 18 are possible, e.g. a spring or any other elastic material.

FIG. 6 shows a perspective view and a front view of a preferred embodiment of an acoustic deflection element 18 surrounded by an index-matching material 36. This embodiment of the deflection element 18 is preferably used in the embodiments of the device 1 shown in FIGS. 2a, 4a-4c and 5. Preferably, the index-matching material 36 is a solid, however, also other materials 36 like liquids, gels and foams can be used. In the present example, the index-matching material 36 has a cylindrical shape, but is not limited to this shape. Preferably, the index-matching material 36 has a refractive index, which is identical or at least similar to the refractive index of the acoustic deflection element 18. In this way, unwanted deflection of the front illumination (see, in particular, FIG. 2a, but also FIGS. 4a-4c and 5) due to refraction at the interface can be avoided or at least reduced. Moreover, both the portion of electromagnetic radiation 6 transmitted through the acoustic deflection element 18 and the portion of acoustic waves reflected by the acoustic deflection element 18 can be increased.

Figure 7:
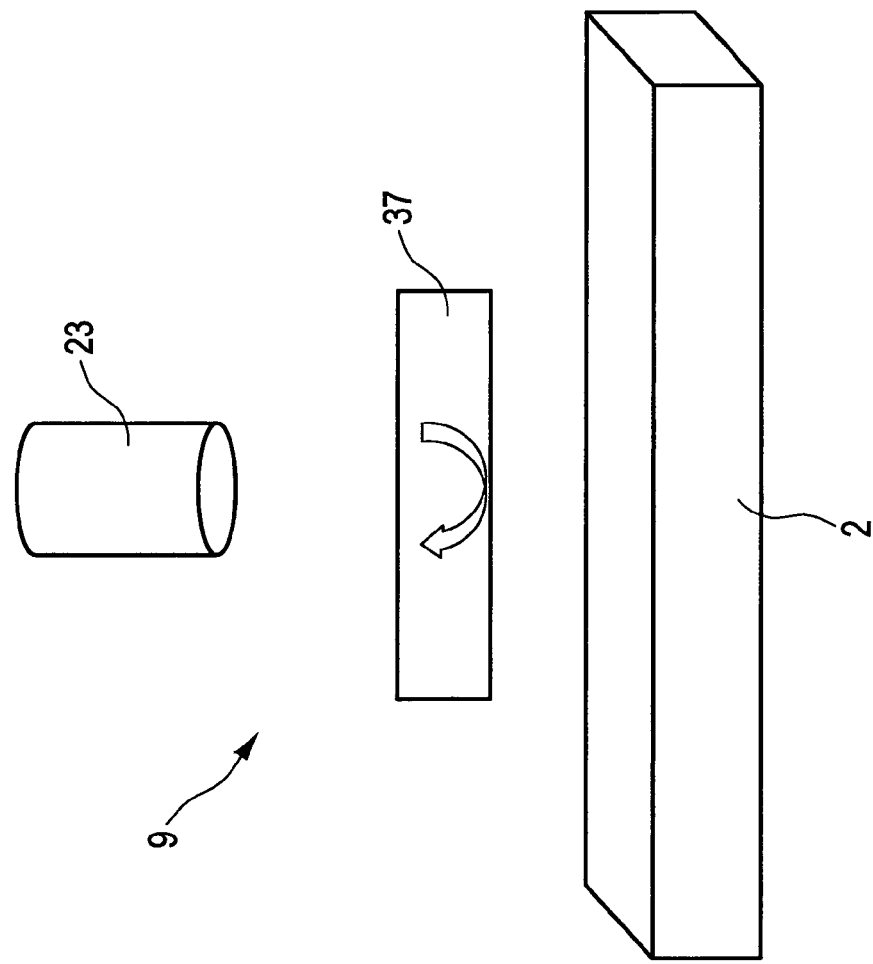
FIG. 7 shows a perspective view of a preferred embodiment of a detection unit using an acoustic refractor.

FIG. 7 shows a perspective view of another preferred embodiment of a detection unit 9 comprising a detection element 23 for detecting acoustic waves and an acoustic refractor 37 configured for guiding acoustic waves emanating from tissue 2 to the detection element 23 by means refraction of the acoustic waves. Preferably, the acoustic refractor 37 is rotatable. The present embodiment may also comprise a plurality of, preferably independently controllable, acoustic refractors 37 for guiding acoustic waves to the detection element 23. The acoustic refractor 37 may also interact with possible other components for guiding acoustic waves, such as acoustic deflection elements, acoustic beam splitters or the like. The present embodiment may also include any number of acoustic beam paths.

Figure 8:
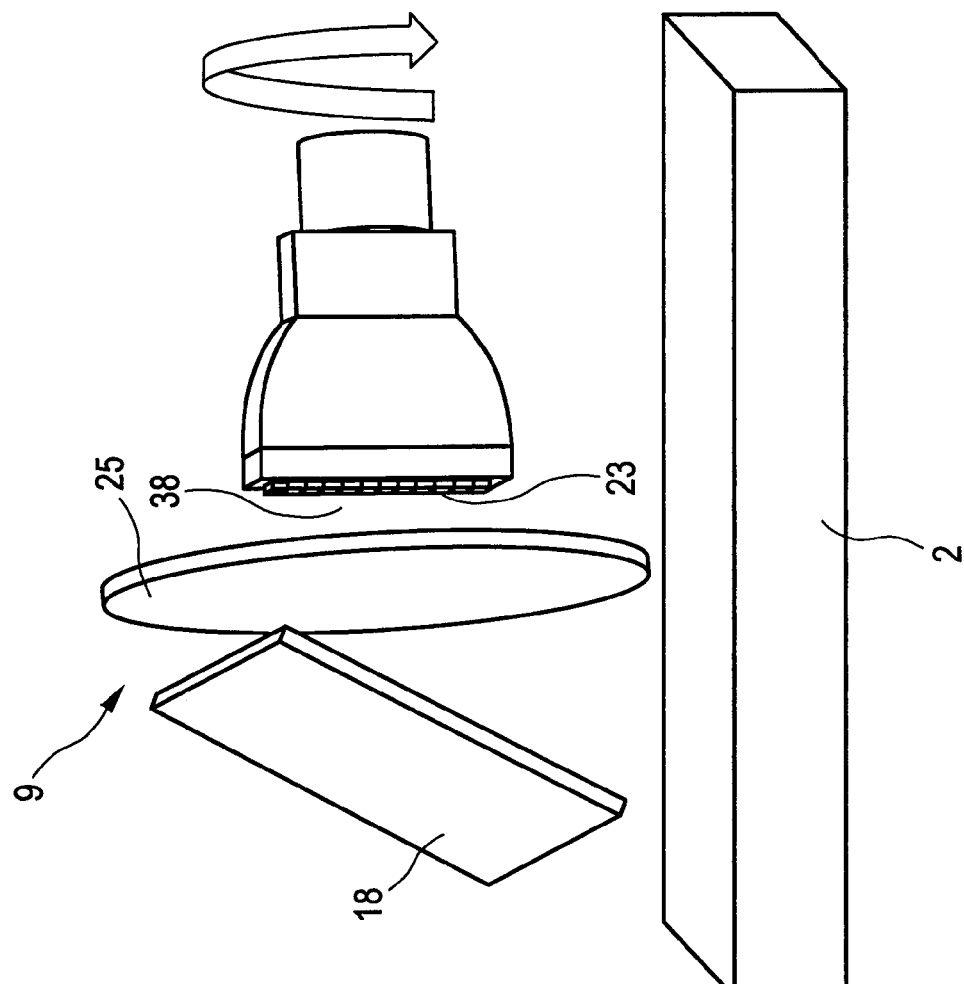
FIG. 8 shows a perspective view of a preferred embodiment of a detection unit using a focusing mechanism.

FIG. 8 shows a perspective view of yet another preferred embodiment of a detection unit 9 using a focusing mechanism. The detection unit 9 comprises an acoustic deflection element 18 for guiding acoustic waves, which emanate from tissue 2, towards a linear array 38 of detection elements 23. Preferably, the array 38 is rotatable around a rotational axis, which is preferably parallel to the surface of the tissue 2, in order to detect acoustic waves originating from differently oriented linear regions of interest of the tissue 2. In addition to the embodiments shown in FIGS. 2a and 4, an acoustic lens 25 is provided for guiding, in particular focusing, acoustic waves which are reflected by the deflection element 18 towards the array 38 of detection elements 23. Instead of only one acoustic lens 25 it is also possible to provide a plurality of acoustic lenses for guiding or focusing acoustic waves towards detection elements 23. Preferably, the acoustic lens 25 exhibits a biconvex shape. Alternatively, also concave or plano-convex shaped lenses are preferred. Instead of an acoustic reflector 18, other components, such as beam splitters, acoustic refractors or the like, can be provided for guiding acoustic waves emanating from tissue 2 towards the acoustic lens 25. Providing one or more acoustic lenses 25 allows for a more compact design of the detection unit 9 and, therefore, an even more efficient packaging of the device.

Figure 10:
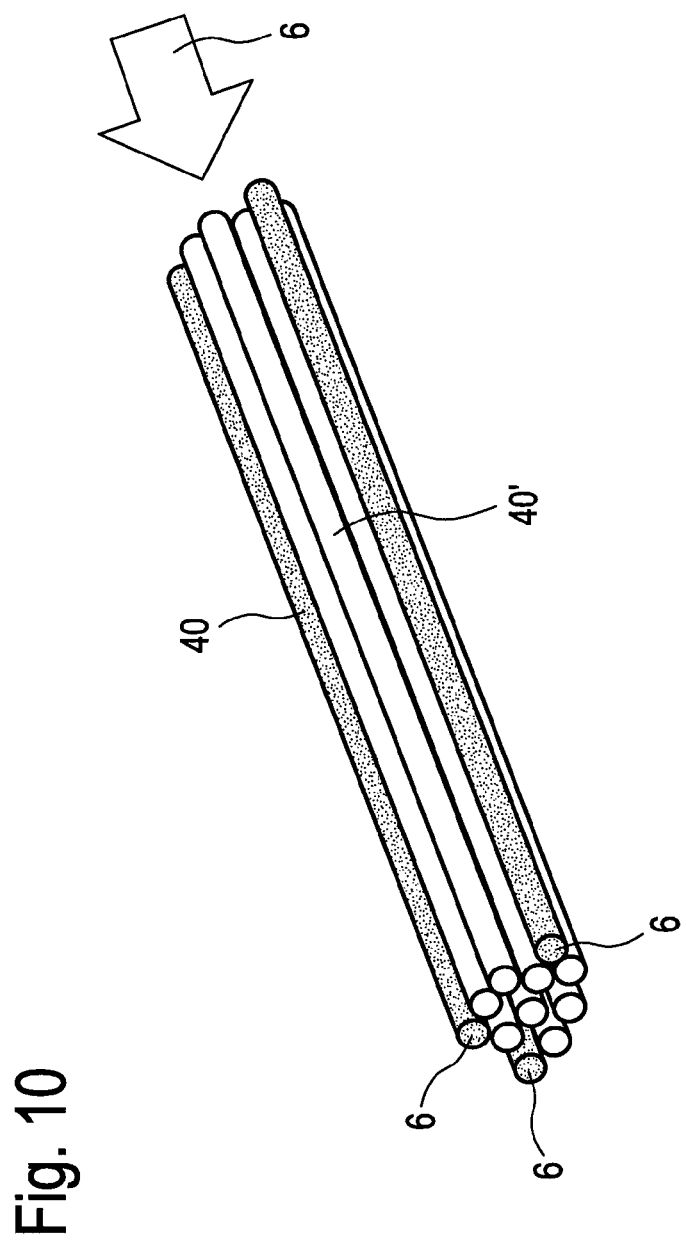
FIG. 10 shows a perspective view of an example of a guiding element of the device for optoacoustic imaging when used in endoscopic applications.

FIG. 10 shows a perspective view of an example of a combined illumination and detection element preferably used in endoscopic applications. In the given example, out of focus detection is implemented in a miniaturized form, wherein ultrasound detection fibers 40' (bright fibers) are used to establish a pinhole pattern.

In a basis unit (not shown) of an according endoscope device, a light source device, a light detector device and an image processing device are provided. Illumination light 6 generated by the light source device is administered to the tissue under investigation through illumination fibers 40 (dark fibers) or any other appropriate fibers inserted within or around a matrix of the detection fibers 40'.

In a particularly preferred embodiment of the inventive device, the scanner operates in frequency domain mode. Frequency domain can be employed to utilize lightweight illumination sources of small form factor that can be integrated in the handheld scanner to improve portability. In frequency domain mode, light with its intensity, frequency or phase modulated over multiple frequencies is directed towards the tissue. The different frequencies can be applied simultaneously or sequentially or in a frequency scanning mode (chirp). Importantly different frequencies can carry different wavelengths. These frequencies can be discrete or being scanned during the imaging session. For example, wavelength 532 nm may be emitted at frequencies 10, 20, 30, . . . 100 MHz, wavelength 580 nm at frequencies 11, 21, 31, . . . 101 MHz and wavelength 630 nm at 12, 22, 32, . . . 102 Mhz. In another example, the intensity of wavelength 550 nm is modulated on a frequency range scanned continuously (chirp) over 5-50 Mhz and the intensity of wavelength 650 nm scanned over the same range but with a time delay so that for example when 550 nm is at 20 MHz, 650 nm is at 5 MHZ. More such wavelengths can be added in a time delayed fashion. The numbers here are used only as example as any combination of wavelength, frequency and frequency range is possible. However by encoding wavelengths at different frequencies it is possible to perform real-time multispectral mesoscopy, since all wavelengths could be emitted towards tissue at the same time.

Detection of sound then collects the amplitude and phase information of the sound waves generated in tissue in response to the intensity modulated illumination, using a pinhole pattern, and reconstructs images at the corresponding optical wavelengths. Detection of the data used in the reconstruction could be based on correlation/auto-correlation functions or on the detection of amplitude and or phase of sound signals, such as homodyne or heterodyne demodulation, quadrature (I&Q) demodulation etc. These signals can be then digitized and the corresponding amplitude and/or phase signals detected or the output of the correlation functions stored for processing and inversion for image generation. This illumination and detection scheme generally utilizes more lightweight and more economic components than time-domain methods (using for example pulsed illumination) and can lead to an cost-efficient device. By employing parallel detection of the data, it can also result in a fast imaging device. Image inversion can then use solutions of the optoacoustic pressure equation in the frequency domain, including back-projection, frequency-domain model based inversion or Fourier Transform inversions possibly implemented using fast fourier transforms. This approach can significantly improve the portability and reduce the cost and speed of a portable optoacoustic device using pinhole technology.

An alternative preferred embodiment uses tissue illumination together with a cMUT detector, whereby the illumination is provided through the CMUT detector, by using small optical gaps in the cMUT wafer which diffract the light onto the object. The delivery of light could be based on fiber illumination, placed in the cMUT wafer openings or by open beam projection. In the latter case, careful arrangement of the cMUT detectors and openings could utilize the cMUT wafer as a meta-material. For example arrays of tiny holes can be manufactured onto the cMUT chip, in the tens of nanometer scales to few microns. These openings could still suffice to effectively pass light onto the tissue. The openings could be effectively blocked with opaque metal cap to further increase the amount of light delivered. Finally the openings could be coated in a gain medium to amplify the light emitted into the object. A preferred illumination nevertheless utilizes side illumination which is incident on tissue by direct deposition occurring between the cMUT wafer and the object imaged. The illumination can be further facilitated by a reflective or diffusive layer, between the cMUT wafer and the object imaged to better propagate the light coming from the side illumination onto tissue, in particular by scattering and/or reflection. The detection of sound waves by the cMUT detector could be facilitated either in the time or the frequency domain.

REFERENCE SIGNS (1) Optoacoustic imaging device
(2) Tissue/Object
(3) Region of interest
(4) Surface of the tissue
(5) Irradiation unit
(6) Electromagnetic radiation/light
(7) Front illumination
(8) Side illumination
(9) Detection unit
(11) Point-like detection element(s)
(12) Field of view
(13) Effective surface/Coupling medium
(14) Casing
(16) Processing device
(18) Acoustic deflection element(s)
(19) Focus point(s)
(20) Fastener/Rim
(21) Port
(22) Array of focus points
(23) Detection element(s)
(24) Ultrasound-opaque element(s)
(25) Acoustic lens
(26) Wavelength filter
(28) Ultrasonic wave-propagating medium
(29) Deflection element rotator
(30) Detection element rotator
(33) Axis of rotation (detection element)
(33') Axis of rotation (deflection element)
(34) Cam
(35) Magnet (on deflection element)
(35') Magnet (fixed in place)
(36) Index-matching material
(37) Acoustic refractor
(38) Array of detection elements
(39) Hand of the user
(40) Optical fibers
(40) Acoustic fibers/waveguides
(41) Cavity
(42) Point-like aperture
(43) Illumination deflecting element

What is claimed is:

1. A device for optoacoustic imaging of an object comprising:
    an irradiation unit having a light source, the irradiation unit irradiating a region of interest of the object with electromagnetic radiation;
    a detection unit comprising one or more detection elements having one or more focus points and focused ultrasound transducers, each focused ultrasound transducer having a focal point, wherein an acoustic lens is not positioned at the focal point, wherein the one or more focus points of the one or more detection elements act as virtual point-like apertures in that only the acoustic waves that pass through the one or more focus points can be detected by the one or more detection elements and the one or more focus points of the one or more detection elements are the respective focal points of the focused ultrasound transducers, the detection unit detecting acoustic waves generated in the region of interest of the object upon irradiation with the electromagnetic radiation, and the detection unit detects the acoustic waves at the one or more focus points; and
    an intermediate surface arranged between the one or more focus points and the object such that the one or more focus points are located outside of the region of interest of the object above a surface of the object, wherein the intermediate surface is configured to be in physical contact with the object during optoacoustic imaging of the object, wherein the intermediate surface creates a fixed distance between the one or more focus points and the surface of the object, and wherein the fixed distance remains constant throughout a data acquisition process.

2. The device according to claim 1, wherein the one or more focus points and the irradiation unit are enclosed in a portable arrangement or portable unit.

3. The device according to claim 1, wherein at least one of the intermediate surface and an enclosure of the device maintain the object in a stable position relative to the intermediate surface such that the object cannot be moved in relation to the intermediate surface during the optoacoustic imaging of the object.

4. The device according to claim 1, wherein the one or more focus points are located a distance of less than 2 mm from the intermediate surface or the surface of the object.

5. The device according to claim 1, each of the one or more focus points exhibiting a divergent field of view in which acoustic waves are collected.

6. The device according to claim 1, the device being a handheld device that is adapted for being grasped and held by a hand in order to position the device onto an object under investigation and to move the device by hand relative to the object under investigation.

7. The device according to claim 1, wherein the one or more detection elements detect the acoustic waves at one or more point-like detection locations being the one or more focus points established by the one or more detection elements.

8. The device according to claim 1, wherein each focal point is established by the focused ultrasound transducer via an acoustic deflection element positioned within a front illumination path.

9. The device according to claim 1, wherein a two-dimensional grid of the focus points is established by the focused ultrasound transducer via a scanning of the focused ultrasound transducer with a two-dimensional miniaturized translation stage.

10. The device according to claim 1, wherein each focal point is established by the focused ultrasound transducer using a curved piezoelectric surface of the focused ultrasound transducer.

11. The device according to claim 1, the detection unit comprising at least one acoustic reflector for deflecting the one or more focus points of the one or more detection elements such that the one or more focus points can be positioned at different lateral locations outside of the region of interest.

12. The device according to claim 11, wherein the acoustic reflector is transparent for at least a part of the electromagnetic radiation irradiated by the irradiation unit.

13. The device according to claim 1, wherein the virtual point-like apertures allow acoustic waves to pass through.

14. The device according to claim 13, wherein the virtual point-like apertures are located such that a major part of an intensity of the acoustic wave at the detection unit passes through the virtual point-like apertures before being detected.

15. A method for optoacoustic imaging of an object by irradiating a region of interest of the object with electromagnetic radiation by means of an irradiation unit having a light source and detecting acoustic waves, which were generated in the region of interest of the object upon irradiation with the electromagnetic radiation, the method comprising:
  detecting the acoustic waves at one or more focus points established by one or more detection elements comprising focused ultrasound transducers, each focused ultrasound transducer establishing a focal point, wherein an acoustic lens is not positioned at the focal point, wherein the one or more focus points established by the one or more detection elements act as virtual point-like apertures in that only the acoustic waves that pass through the one or more established focus points can be detected by the one or more detection elements, and wherein the one or more focus points established by the one or more detection elements are the focal points established by the focused ultrasound transducers, and
  arranging an intermediate surface between the one or more established focus points and the object, wherein the one or more established focus points are located outside of the region of interest of the object above a surface of the object, and the intermediate surface is configured to be in physical contact with the object, wherein the intermediate surface creates a fixed distance between the one or more established focus points and the surface of the object, and wherein the fixed distance remains constant throughout a data acquisition process.

16. The method of claim 15, wherein said virtual point-like apertures are implemented using detector arrays or detectors shaped to reject signals.

17. The method of claim 15, wherein each focal point is established by the focused ultrasound transducer via an acoustic deflection element positioned within a front illumination path.

18. The method of claim 15, wherein a two-dimensional grid of the focus points is established by the focused ultrasound transducer via a scanning of the focused ultrasound transducer with a two-dimensional miniaturized translation stage.

19. The method of claim 15, wherein each focal point is established by the focused ultrasound transducer using a curved piezoelectric surface of the focused ultrasound transducer.

* * * * *